United States Patent
Thompson

(10) Patent No.: US 12,257,231 B2
(45) Date of Patent: *Mar. 25, 2025

(54) METHOD AND COMPOSITION FOR PREVENTING AND TREATING VIRAL INFECTIONS

(71) Applicant: Global BioLife Inc., Bethesda, MD (US)

(72) Inventor: Daryl L. Thompson, Winter Haven, FL (US)

(73) Assignee: Global BioLife Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/346,569

(22) Filed: Jun. 14, 2021

(65) Prior Publication Data

US 2021/0299088 A1 Sep. 30, 2021

Related U.S. Application Data

(63) Continuation-in-part of application No. 16/544,308, filed on Aug. 19, 2019, now Pat. No. 11,033,528, which is a continuation of application No. 15/043,472, filed on Feb. 12, 2016, now Pat. No. 10,383,842.

(60) Provisional application No. 62/115,983, filed on Feb. 13, 2015.

(51) Int. Cl.

| | |
|---|---|
| *A61K 31/352* | (2006.01) |
| *A61K 9/00* | (2006.01) |
| *A61K 9/20* | (2006.01) |
| *A61K 9/48* | (2006.01) |
| *A61K 31/353* | (2006.01) |
| *A61K 31/4453* | (2006.01) |
| *A61K 47/16* | (2006.01) |
| *A61K 47/22* | (2006.01) |
| *A61P 31/16* | (2006.01) |

(52) U.S. Cl.
CPC .......... *A61K 31/352* (2013.01); *A61K 9/0019* (2013.01); *A61K 9/2013* (2013.01); *A61K 9/4858* (2013.01); *A61K 31/353* (2013.01); *A61K 31/4453* (2013.01); *A61K 47/16* (2013.01); *A61K 47/22* (2013.01); *A61P 31/16* (2018.01)

(58) Field of Classification Search
CPC .. A61K 31/352; A61K 31/353; A61K 9/4858; A61K 9/2013; A61K 9/0019; A61K 47/16; A61K 47/22; A61P 31/16
See application file for complete search history.

(56) References Cited

U.S. PATENT DOCUMENTS

2012/0022010 A1* 1/2012 Brand ................. A61P 31/22
514/320
2019/0365703 A1* 12/2019 Thompson ............. A61K 47/16

OTHER PUBLICATIONS

Lin et al., Antiviral Research, 2005, 68, p. 36-42. (Year: 2005).*
Yu et al., Bioorganic & Medicinal Chemistry Letters, 2012, 22, p. 4049-4054. (Year: 2012).*
Guler et al., Archives of Microbiology, 2021, 203, p. 3557-3564, Published online: May 5, 2021. (Year: 2021).*
Choi et al., Journal of Nutrition, 2004, 134(5), p. 1013-1019. (Year: 2004).*
Garg et al., Phytotherapy Research, 2001, 15, p. 655-669. (Year: 2001).*
Feng et al., Molecules, 2014, 19, p. 5624-5633, published Apr. 30, 2014. (Year: 2014).*
Office Action dated Feb. 27, 2023 in corresponding U.S. Appl. No. 17/346,602.

* cited by examiner

Primary Examiner — Jonathan S Lau

(74) Attorney, Agent, or Firm — Stephen J. Weyer, Esq.; Stites & Harbison, PLLC

(57) ABSTRACT

A method and composition for treating viral infections using a combination of naturally occurring compounds is provided. The method includes administering to a patient at risk of or diagnosed with a viral infection a composition including therapeutically effective amounts of a myricetin and hesperitin to treat viral infections include coronavirus.

11 Claims, 32 Drawing Sheets

Equivir/Nemovir

Myricetin

Polyphenol found in vegetables, fruits, nuts, berries, tea, and red wine

Point-source intracellular inhibition

Inhibits TNF-α, which drives ICAM-1 expression

Down regulates
- ICAM-1
- Helicase
- Neuraminidase

Hesperetin

Polyphenol found in citrus fruits

Extracellular inhibition

Partially migrates to skin, lung, and nasal tissue

Down regulates
- TNF-α
- ICAM-1
- VCAM-1
- ATPase

- IL-1β
- IL-6
- IL-8
- IL-12

Piperine

Alkaloid found in black pepper

Increases trans-membrane permeability/bioavailability

FIG. 2

Cytotoxicity of Equivir treated SARS-CoV-2 infected Vero E6 Cells D3

Compound Concentration (μl/mL)

Representative images of Treated Calu-3 from D2/D3 (48/72hr PI)
-2hr group: Treatments were added to cells 2 hours prior to infection with SARS-CoV-2.

Untreated/uninfected

Equivir 200 µg/ml treated cells 48 / 72 hours

Equivir 150 µg/ml treated cells 48 / 72 hours

Equivir 100 µg/ml treated cells 48 / 72 hours

Equivir 50 μg/ml treated cells 48 / 72 hours

Equivir 25 μg/ml treated cells 48 / 72 hours

Equivir (200 μg/ml) + Gallic Acid (20 μg/ml)

Equivir (150 μg/ml) + Gallic Acid (15 μg/ml)

Equivir (100 μg/ml) + Gallic Acid (10 μg/ml)

Equivir (50 μg/ml) + Gallic Acid (5 μg/ml)

Equivir (25 µg/ml) + Gallic Acid (2.5 µg/ml)

+2hr Group: Treatment was added 2 hours after infection with SARS-CoV-2
Equivir 200 µg/ml +2hr Group: Treatment was added 2 hours after infection with SARS-CoV-2
Equivir 150 µg/ml +2hr Group: Treatment was added 2 hours after infection with SARS-CoV-2
Equivir 100 µg/ml +2hr Group: Treatment was added 2 hours after infection with SARS-CoV-2
Equivir 50 µg/ml +2hr Group: Treatment was added 2 hours after infection with SARS-CoV-2
Equivir 25 µg/ml +2hr Group: Treatment was added 2 hours after infection with SARS-CoV-2
Equivir (200 μg/ml) + Gallic Acid (20 μg/ml)

+2hr Group: Treatment was added 2 hours after infection with SARS-CoV-2
Equivir (150 μg/ml) + Gallic Acid (15 μg/ml)

+2hr Group: Treatment was added 2 hours after infection with SARS-CoV-2
Equivir (100 μg/ml) + Gallic Acid (10 μg/ml)

+2hr Group: Treatment was added 2 hours after infection with SARS-CoV-2
Equivir (50 µg/ml) + Gallic Acid (5 µg/ml)

+2hr Group: Treatment was added 2 hours after infection with SARS-CoV-2
Equivir (25 µg/ml) + Gallic Acid (2.5 µg/ml)

METHOD AND COMPOSITION FOR PREVENTING AND TREATING VIRAL INFECTIONS

RELATED APPLICATIONS

This application claims priority to U.S. Pat. No. 11,033,528 issued on Jun. 15, 2021 from U.S. application Ser. No. 16/544,308, which claims priority to U.S. Pat. No. 10,383,842 that issued on Aug. 20, 2019, which in turn claims priority to U.S. Provisional Application No. 62/115,983 filed Feb. 13, 2015, the entire contents of all hereby incorporated by reference as though fully set forth herein.

FIELD OF THE INVENTION

The present disclosure relates generally to preventing and treating viral infections, and more particularly to a composition including a helicase ATPase inhibitor, a sialidase enzyme inhibitor, an ICAM-1 Inhibitor and TNF-α inhibitor to down regulate the immune cytokine response, administered to a patient at risk of or diagnosed with a viral infection.

BACKGROUND

Many human diseases result from infection by microscopic organisms called viruses. Infection by viruses can give rise to symptoms that vary from mild to severe. Viral infections can result in large numbers of deaths. Examples of such pandemics include the Spanish flu of 1918-1919 that killed approximately 40 million people and the HIV/AIDS epidemic that has killed almost 2 million people.

Viruses require host organisms in order to replicate and viruses are transmitted from an infected host to an uninfected host through a number of mechanisms. A virus will first attach itself to a host cell. It will then enter the cell and release its genetic code (i.e., RNA or DNA). The virus makes use of the host cell's functional proteins and enzymes in order to replicate. Eventually, the host cell may die because the mechanisms it needs to survive are controlled by the virus. After death of the cell, the replicated viruses are released, allowing them to attack new host cells and continuing the replication process. Some viruses cause modification of the host cells leading to cancer, while other viruses can remain dormant in the host for an extended period prior to the infection becoming symptomatic in the host.

The symptoms that result from viral infections can vary from virus-to-virus as any one virus typically will infect only certain types of cells. This observation also means that a specific virus will typically infect only certain species, although mutation of a virus can allow it to extend the number of species that any one virus is able to infect.

Host species have developed a number of defense mechanisms to protect themselves from viral infections. The first lines of defense are mechanisms that prevent viral entry into the host. The skin provides an impermeable barrier to entry. Viruses typically enter the body through body cavities and can pass through the mucosal surfaces that line these cavities. Once a virus is in the body and detected by the body's immune system, lymphocytes and monocytes in the blood learn how to attack the invader. Invaded cells release cytokines such as the interferons (for example IL 1, IL 6, IL 12, IL 16), tumor necrosis factor (TNF-α), and interferons (typically interferons a and g). The role of these cytokines is to increase the resistance of other host cells to the invading virus. Many of the symptoms of viral infection experienced by the host results from the extensive release of cytokines, commonly referred to as the cytokine storm.

The white blood cells are able to remember how to combat viruses that have previously invaded the body. So if the host survives the initial attack of the virus, the immune system is able to respond much more quickly to subsequent infections of the same virus. The body has developed an immunity to the virus. Such immunity can also be induced by presenting the immune system with a surrogate (vaccine) for the virus in a process known as immunization.

Antiviral drugs are known in the art to assist the immune system in overcoming a viral infection in a patient. Most antiviral drugs work by slowing the replication of the virus in the infected patient's body thus allowing the body's immune system to launch an effective response when the disease symptoms are less severe. Antiviral drugs may work specifically on one or two viruses or may be effective across a broad spectrum of viruses. There are many known mechanisms by which antiviral agents can slow viral replication. One antiviral strategy is to slow or prevent the virus infiltrating a target cell, for example by binding to a receptor on the target cell which is required by the virus to enter the cell or by coating the virus so preventing its ability to bind to the target receptor(s). Other antiviral agents can slow viral replication once the virus particle has entered the target cell. Such mechanisms are well known in the art.

BRIEF SUMMARY OF THE INVENTION

The present invention is directed to treating viral infections such as coronavirus using a therapeutically effective amount of a composition comprising myricetin and hesperitin referred here throughout this disclosure as "Equivir". The coronavirus includes but is not limited to SARS-CoV-2 (COVID-19) as well as other coronaviruses. A combination of myricetin and hesperitin have an effect of downregulating TNF-α in a subject or host to which the combination is administered.

The composition of myricetin and hesperitin is effective in combating a viral infection by reducing replication rates for the virus and by reducing the virus's ability to stimulate the immune response of the host, thereby preserving cellular integrity. Specifically, the composition is effective in inhibiting the ATPase activity of the replication enzyme helicase on the cell surface by docking site competition. Moreover, the composition is effective in inhibiting sialidase and ICAM-1 enzymes, which are involved in the entry and release stages of intercellular virus particles.

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

In one aspect of the invention there is provided a method of preventing and treating viral infections including administering a composition including therapeutically effective amounts of a helicase ATPase inhibitor, a sialidase enzyme inhibitor and ICAM-1 inhibitor to a patient at risk of or diagnosed with a viral infection.

In another aspect of the invention there is provided a composition for treating viral infections including therapeutically effective amounts of a helicase ATPase inhibitor, a sialidase enzyme inhibitor and ICAM-1 inhibitor.

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

In another embodiment, the helicase ATPase inhibitor includes a naturally occurring compound, a synthetic derivative of a naturally occurring compound or a combination thereof.

In another embodiment, the naturally occurring ATPase inhibitor compound includes a flavonoid, a flavonoid derivative or a combination thereof.

In another embodiment, the flavonoid ATPase inhibitor is myricetin.

In another embodiment, the I-CAM 1 inhibitor includes a flavonoid, a flavonoid derivative or a combination thereof.

In another embodiment, the ICAM-1 inhibitor is myricetin.

In another embodiment, the sialidase enzyme inhibitor includes a naturally occurring compound, a synthetic derivative of a naturally occurring compound or a combination thereof.

In another embodiment, the naturally occurring sialidase enzyme inhibitor compound includes a flavonoid, a flavonoid derivative or a combination thereof.

In another embodiment, the flavonoid sialidase enzyme inhibitor is hesperitin or hesperidin.

In another embodiment, the viral infection is the Ebola virus or rhinovirus.

In another embodiment, the viral infection is influenza.

In another embodiment, the patient is a human.

In another embodiment, the composition further includes a permeation enhancer.

In another embodiment, the permeation enhancer is piperine.

In another embodiment, the composition further includes piperine.

In another embodiment, about 300 to about 700 mg myricetin; about 100 to about 500 mg hesperitin; and about 5 to about 100 mg piperine are present in the composition.

In another embodiment, about 450 to about 600 mg myricetin; about 250 to about 400 mg hesperitin; and about 5 to about 50 mg piperine are present in the composition.

In another embodiment, about 55 to about 75% weight myricetin; about 30 to about 50% hesperitin; and about 0.5 to about 5% piperine, based on the total weight of the mixture, is present in the composition.

In another embodiment, the ratio of piperine, myricetin and hesperitin present in the composition is about 1:(30-60):(30-60).

In another aspect of the invention there is provided a method of preventing and treating coronavirus in a human including administering a composition including 60% myricetin, 39% hesperitin and 1% piperine, based on the total weight of the mixture, to a human at risk of or diagnosed with a the coronavirus.

In another aspect of the invention there is provided a composition for preventing and treating the coronavirus including 60% myricetin, 39% hesperitin and 1% piperine, based on the total weight of the mixture.

BRIEF DESCRIPTION OF THE DRAWINGS

FIG. 2 illustrates effects myricetin, hesperitin and piperine have on metabolic processes.

FIG. 8 is a graph showing cytotoxicity of Equivir treated SARS-CoV-2.

Figure 11:
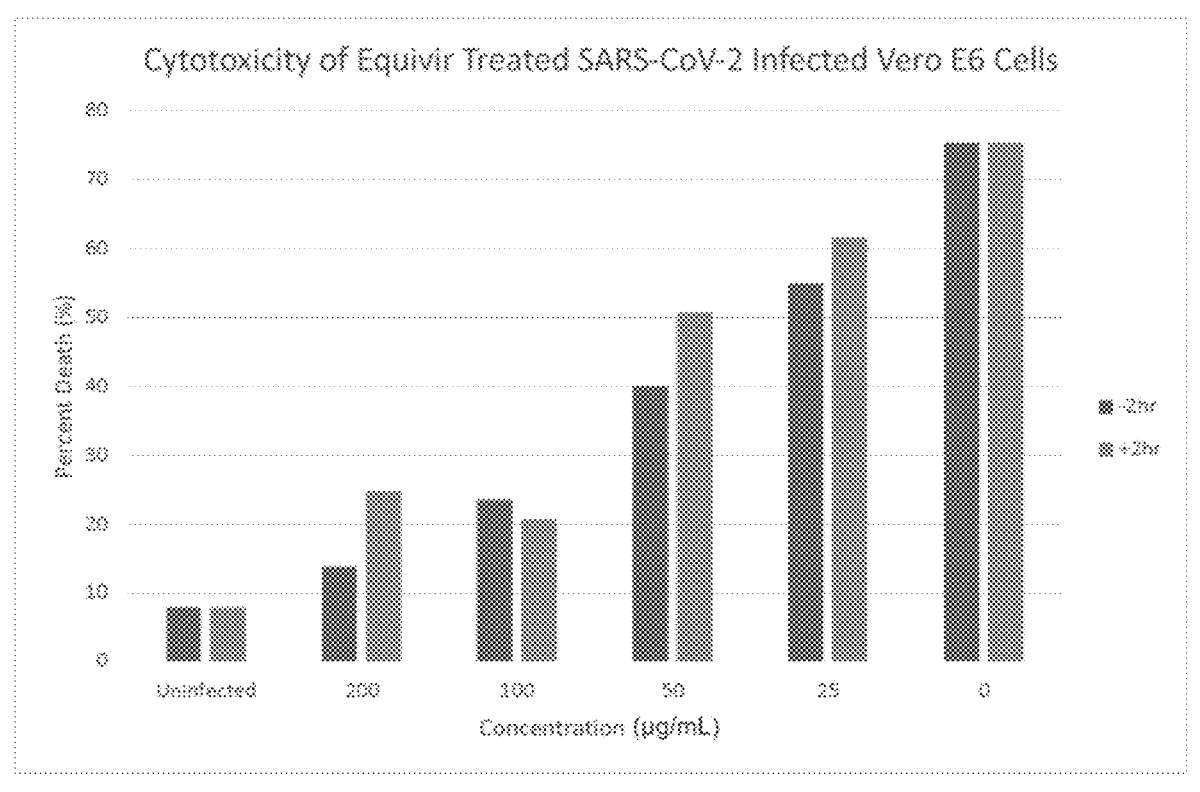

FIG. 11 is a graph comparing percent cell death versus Equivir concentration at under 2 hours and over 2 hours.

DETAILED DESCRIPTION

Figure 1:
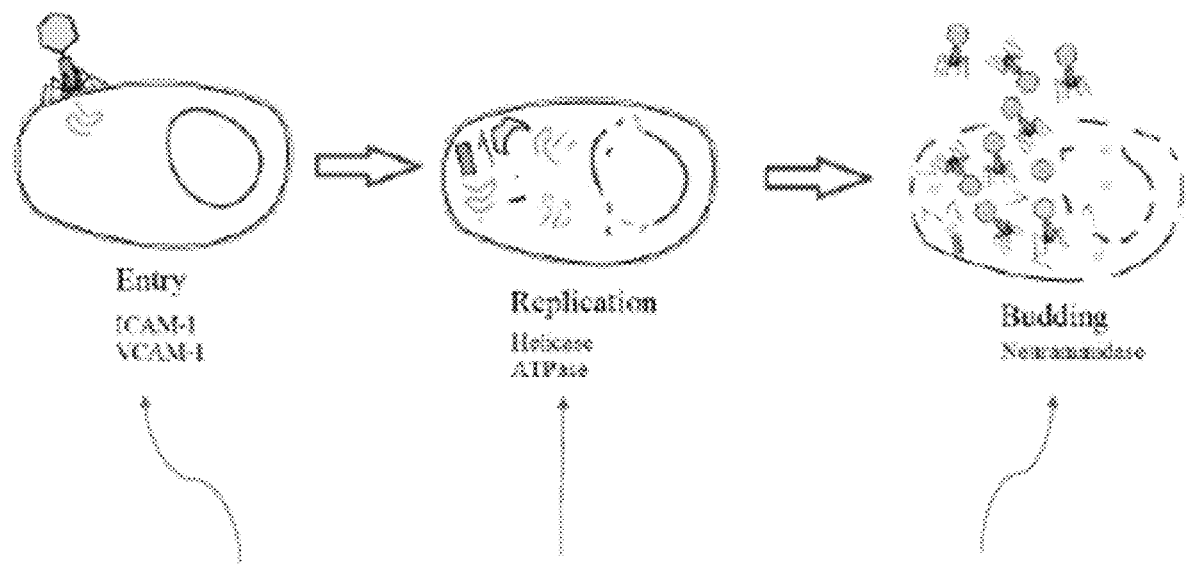
FIG. 1 shows a synergistic effect of Equivir on virus replication.

As used herein, the following terms and phrases shall have the meaning set forth below.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been created or modified by man.

"Treating" a condition or disease refers to curing as well as ameliorating at least one symptom of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the patient and disease or condition being treated, the weight and age of the patient, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

The term "pharmaceutically acceptable carrier" means a carrier or diluent that does not give a stimulus to an organism and destroy the natures and bioactivities of an administered compound.

The present invention, in one form is directed to a therapeutic treatment which combines myricetin and hesperitin (chemical structures of both shown below) to treat viral infections including coronavirus.

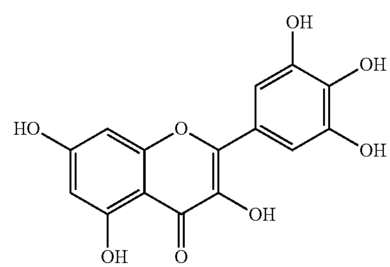

Myricetin

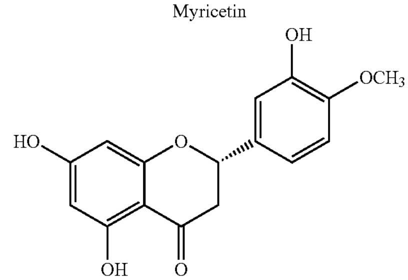

Hesperitin

Referring generally to FIG. 1 there is a synergistic effect of myricetin plus hesperitin in blocking or negatively effecting a viral replication cycle.

The present invention is directed to administering a composition comprising therapeutically effective amounts of a helicase ATPase inhibitor, a sialidase enzyme inhibitor and ICAM-1 inhibitor to a patient at risk of or diagnosed with a viral infection.

In one embodiment, the effective concentration for a composition consisting of a mixture by weight of a helicase ATPase inhibitor, a sialidase enzyme inhibitor and ICAM-1 inhibitor ranges from about 250 mg to about 100 mg of the composition. In one embodiment, a single dose per day, taken at the beginning of the day, is about 750 mg, or about 1500 mg. In another embodiment, the composition is administered as a dose three times a day in an amount of about 750 mg per dose. The total amount of the composition administered daily, in one embodiment is at least 500 mg, or at least 750 mg, or at least 100 mg or at least 2500 mg.

The helicase ATPase inhibitor of the present invention functions as a cellular replication inhibitor by inhibiting the ATPase activity of the replication enzyme helicase on the cell surface by docking site competition. This inhibition reduces viral un-packaging and replication rates and reduces mutation of viral strain due to the inhibiting activity taking place outside the cell.

In one embodiment, the helicase ATPase inhibitor includes a naturally occurring compound, a synthetic derivative of a naturally occurring compound or a combination thereof. There are several naturally occurring compounds that have an effect on viral infections.

In one embodiment, the naturally occurring ATPase inhibitor compound comprises a flavonoid, a flavonoid derivative or a combination thereof. Flavanoids are naturally-occurring antioxidant compounds for which several therapeutic uses have been demonstrated including diabetes, neurological disorders, thrombin inhibition, cancer, and antivirals. Generally, flavonoids generate few side-effects when administered and can safely be provided to patients in large doses. Two types of flavonoids that are useful are flavanones and flavones. Flavanones have the structure (I) shown below and flavones have the similar structure (II) shown below:

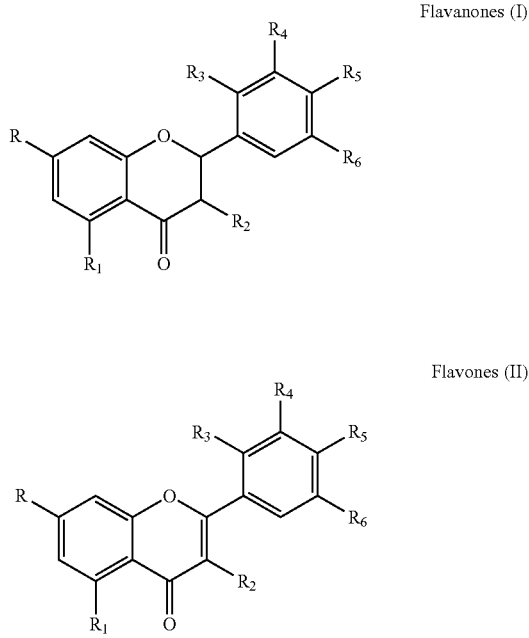

Flavanones (I)

Flavones (II)

wherein R, $R_1$, $R_2$, $R_3$, $R_4$, $R_5$ and $R_6$ are each independently hydrogen, a hydroxy group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. Several examples of the flavonoids of formula (I) and (II) are shown below in the table below.

TABLE

| | R | Ri | R2 | $R_3$ | $R_4$ | $R_5$ | $R_6$ |
|---|---|---|---|---|---|---|---|
| FLAVONE | | | | | | | |
| Flavone | H | H | H | H | H | H | H |
| Chrysin | OH | OH | H | H | H | H | H |
| Apigenin | OH | OH | H | H | H | OH | H |
| Luteolin | OH | OH | H | H | H | OH | H |
| Diosmin | -0-rutinose | OH | H | H | OH | OCH$_3$ | H |
| Fisetin | OH | H | OH | H | OH | OH | H |
| Kaempferol | OH | OH | OH | H | H | OH | H |
| Morin | OH | OH | OH | OH | H | OH | H |
| Quercetin | OH | OH | OH | H | OH | OH | H |
| Myricetin | OH | OH | OH | H | OH | OH | OH |
| Rutin | OH | OH | -0-rutinose | H | OH | OH | H |
| Rhoifolin | R-G-$^a$ | OH | H | H | H | OH | H |
| FLAVANONE | | | | | | | |
| Galang in | OH | OH | OH | H | H | H | H |
| Hesperetin | OH | OH | H | H | OH | OCH$_3$ | H |
| Eriodictyol | OH | OH | H | H | OH | OH | H |
| Naringenin | OH | OH | H | H | H | OH | H |
| Naringin | R-G-$^a$ | OH | H | H | H | OH | H |
| Neohesperidin | R-G-$^b$ | OH | H | H | OH | OCH$_3$ | H |

| FLAVANONE | R | Ri | $R_2$ | $R_3$ | $R_4$ | $R_5$ | $R_6$ |
|---|---|---|---|---|---|---|---|
| Hesperidin | R-G-$^b$ | OH | H | H | OH | OCH$_3$ | H |
| Narirutin | R-G-$^b$ | OH | H | H | H | OH | H |
| Prunin | Glucose- | OH | H | H | H | OH | H |

$^a$rhamnose-glucose, L-rhamnose is linked a 1→2 to D-glucose
$^b$rhamnose-glucose, L-rhamnose is linked a 1→6 to D-glucose In one embodiment, the helicase ATPase inhibitor is the flavonoid myricetin.

Myricetin is a flavonoid found in most berries, including cherry, cranberry and bilberry, and other plants, including parsley and rutabagas. In addition to inhibiting the enzyme helicase, myricetin functions as a powerful and broad cytokine signaling inhibitor and immune-modulator. Myricetin down-regulates cytokine activity and TNF-α. This includes, for example, lymphokines, interleukines and chemokines, particularly interleukins IL-IL-36 and TNF-α.

Naturally occurring flavonoids, such as myricetin, are commonly substituted at variable positions, mainly by hydroxyl, methoxyl, isoprenyl and glycosyl groups. The introduction of halogens in these molecules show strong biological activities, including antiviral properties.

The ICAM-1 inhibitor of the present invention functions to slow viral replication inside the cell by inhibiting the ICAM-1 enzyme, which is involved in entry and release stages of intercellular virus particles.

In one embodiment, the ICAM-1 inhibitor is the flavonoid myricetin.

The sialidase of the present invention functions to slow viral replication inside the cell by inhibiting the sialidase enzyme, which is involved in entry and release stages of intercellular virus particles.

In one embodiment, the sialidase enzyme inhibitor comprises a naturally occurring compound, a synthetic derivative of a naturally occurring compound or a combination thereof. In another embodiment, the naturally occurring sialidase enzyme inhibitor compound comprises a flavonoid, a flavonoid derivative or a combination thereof.

In one embodiment, the sialidase enzyme inhibitor is the flavonoid hesperitin or hesperidin. Hesperidin is a flavonoid found in plants, mainly in citrus fruit peels.

Hesperitin is the aglycone form of hesperidin. In addition to inhibiting the sialidase enzyme, hesperitin and hesperidin function as cellular integrity agents by inhibiting cellular stratum acidification due to excessive histamine and histadine concentrations. Hesperitin and hesperidin further prevent integrin loss by inhibition of intracellular $H_2O_2$ production as well as activation of nuclear factor kB, phosphorylation of IkB (alpha), and inhibition of P-38 MAPK (mitogen activated kinase). Hesperitin and hesperidin further enhance cellular integrity by stimulating fibroblast collagen synthesis with associated enhancement of migration and proliferation.

The following summarizes the effectiveness of myricetin plus hesperitin ("Equivir") against SARS-CoV-2 also known as COVID-19 as follows:

COVID-19 effective inhibition as treatment at 50 µg/ml;

COVID-19 effective inhibition as post-exposure treatment at 100 µg/ml; and

COVID-19 effective as a prophylactic at 100 µg/ml.

Further, Equivir has effects to downregulate various metabolic processes as shown in FIG. 2.

In one embodiment, a single dose per day, taken at the beginning of the day, is about 750 mg, or about 1500 mg. In another embodiment, the composition is administered as a dose three times a day in an amount of about 750 mg per dose. The total amount of the composition administered daily, in one embodiment is at least 500 mg, or at least 750 mg, or at least 100 mg or at least 2500 mg.

Myricetin when administered to a host acts in some instances as a helicase ATPase inhibitor and/or as an ICAM-1 inhibitor. For example, myricetin (acting as a helicase ATPase inhibitor) functions as a cellular replication inhibitor by inhibiting the ATPase activity of the replication enzyme helicase on the cell surface by docking site competition. This inhibition reduces viral unpackaging and replication rates and reduces mutation of viral strain due to the inhibiting activity taking place outside the cell.

Myricetin is a flavonoid found in most berries, including cherry, cranberry and bilberry, and other plants, including parsley and rutabagas. In addition to inhibiting the enzyme helicase, myricetin functions as a powerful and broad cytokine signaling inhibitor and immune-modulator. Myricetin down-regulates cytokine activity and TNF-α. This includes, for example, lymphokines, interleukines and chemokines, particularly interleukins IL-IL-36 and TNF-α.

Naturally occurring flavonoids, such as myricetin, are commonly substituted at variable positions, mainly by hydroxyl, methoxyl, isoprenyl and glycosyl groups. The introduction of halogens in these molecules show strong biological activities, including antiviral properties.

As noted above, myricetin can act as an ICAM-1 inhibitor to slow viral replication inside the cell by inhibiting the ICAM-1 enzyme, which is involved in entry and release stages of intercellular virus particles.

Hesperitin acts as a sialidase enzyme inhibitor, in accordance with the present disclosure to slow viral replication inside the cell by inhibiting the sialidase enzyme, which is involved in entry and release stages of intercellular virus particles.

Hesperitin is the aglycone form of hesperidin. In addition to inhibiting the sialidase enzyme, hesperitin and hesperidin function as cellular integrity agents by inhibiting cellular stratum acidification due to excessive histamine and histadine concentrations. Hesperitin and hesperidin further prevent integrin loss by inhibition of intracellular $H_2O_2$ production as well as activation of nuclear factor kB, phosphorylation of IkB(alpha), and inhibition of P-38 MAPK (mitogen activated kinase). Hesperitin and hesperidin further enhance cellular integrity by stimulating fibroblast collagen synthesis with associated enhancement of migration and proliferation.

The present invention prevents and treats a wide variety of virus infections including, but not limited, to cowpoxvirus, herpesviridae, herpes simplex viruses, Epstein-Barr virus, human adenoviruses, human papillomaviruses, hepatitis B virus, retroviridae (such as human immunodeficiency virus), rotavirus, filoviridae (such as Marburg virus and Ebola viruses), dengue virus, influenza viruses, hanta virus, Severe Acute Respiratory Syndrome coronavirus (SARS), enteroviruses, rhinovirus, hepatitis virus, norovirus, Norwalk virus, Alpha viruses, Chikungunya virus, Venezuelan equine encephalitis virus, Western equine encephalitis virus, Eastern equine encephalitis virus, St. Louis encephalitis virus, West Nile virus, yellow fever virus, and Creutzfeldt-Jakob-Disease, arbovirus, flavivirus and RNA viruses.

There are several methods by which myricetin, hesperitin or hesperidin may be harvested from their original botanical sources. In one method, for example, extraction from botanical sources begins with a suitable seed material such as grape seeds or tomato seeds, pine bark or citrus rinds. The source material is macerated and flushed with water to separate the water soluble flavonoids from the bulkier pectins and fibers of the source material. This pulp wash is then treated with appropriate acids and bases as known in the art to cause precipitation. The precipitate is then washed again, dried and then concentrated to yield a fairly pure flavonoid composition. This composition may be further clarified to yield fractions containing the desired flavonoid product.

In another method, reverse osmosis may be used to remove the target flavonoid by filtering it out of juice streams from beverage manufacturing processes. The process of manufacturing fruit juices such as citrus, liberates the flavonoids from the rind and suspends them in the juice product. It is often desirable to remove these water soluble flavonoids because of their tendency to produce bitter or off flavors in the juice product.

For example, during the manufacture of grapefruit juice, the primary grapefruit flavonoid naringin is released into the juice stream. Because naringin has a very distinct bitter taste, it is necessary to remove it from the product stream via the use of resin coated reverse osmosis devices to restore the proper flavor profile of the grapefruit juice. The resultant flavonoid is finally collected and dried to yield a fairly pure product.

The flavonoids may also be manufactured by synthetic methods. Such methods may include an Allan-Robinson Reaction, which is a chemical reaction of o-hydroxylaryl ketones with aromatic anhydrides to form flavanones. Another example is Auwers Synthesis, which is a procedure that requires an acid catalyzed aldol condensation between benzaldehyde and a 3-oxypentanon to an o-hydroxychalcone. Further bromination of the alkene group gives a dibromo-adduct that rearranges to a flavanol by reaction with potassium hydroxide. A further example is a Baker-Venkataraman Rearrangement, which involves the reaction of 2-acetoxyacetophenones with base to form 1,3-diketones. The rearrangement reaction proceeds via enolate formation followed by an acyl transfer to form flavanones. An Algar-Flynn-Oyamada Reaction may also be used. In this reaction, a chalcone undergoes an oxidative cyclization to form a flavanol.

The composition of the present invention may be administered to patients at risk of viral infection, for example through exposure to patients known or suspected of having a viral disease, in order to prevent or lessen the severity of symptoms following infection and/or reduce the possibility of severe symptoms or death following infections.

The composition of the present invention may be administered to patients known or suspected of having a viral disease, in order to lessen the severity of symptoms and/or reduce the possibility of severe symptoms or death.

In one embodiment, the patient is a human. In other embodiments, the patient may be a mammal other than a human, such as a dog.

In one embodiment, the composition further includes a permeation enhancer. The permeation enhancer of the present invention functions to enhance oral uptake or cellular uptake of the helicase ATPase inhibitor, ICAM-1 enzyme inhibitor and the sialidase enzyme inhibitor.

In one embodiment, the permeation enhancer is piperine. Piperine (structure below) is an alkaloid and is responsible for the pungency of black pepper and long pepper.

Piperine

Piperine is commercially available or may be extracted from black pepper using dichloromethane. Piperine increases the bioavailability of nutrients.

In one embodiment, the composition includes about 300 to about 700 mg myricetin; about 100 to about 500 mg hesperitin; and about 5 to about 100 mg piperine. In another embodiment, the composition includes about 450 to about 600 mg myricetin; about 250 to about 400 mg hesperitin; and about 5 to about 50 mg piperine.

In one embodiment, the composition includes a mixture of about 50 to about 80% weight myricetin; about 25 to about 55% hesperitin; and about 0.5 to about 10% piperine, based on the total weight of the mixture. In another embodiment, the composition includes a mixture of about 55 to about 75% weight myricetin; about 30 to about 50% hesperitin; and about 0.5 to about 5% piperine, based on the total weight of the mixture. In yet another embodiment, the composition includes a mixture of about 60% myricetin; about 39% hesperitin; and 1% piperine, based on the total weight of the mixture.

In one embodiment, the composition includes a ratio of piperine to myricetin to hesperitin of about 1:(2-4):(2-4), or about 1:(2-3):(2-3), or about 1:3:3. In another embodiment, the composition includes a ratio of piperine to myricetin to hesperitin of about 1:(20-75):(20-75), or about 1:(30-60):(30-60), or about 1:(40-55):(40-55).

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, each containing a predetermined amount of a compound of the present invention as an active ingredient.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the pharmaceutical compositions may also comprise buffering agents.

Embodiments of inventive compositions and methods are illustrated in the following examples. These examples are provided for illustrative purposes and are not considered limitations on the scope of inventive compositions and methods.

EXAMPLES

The present composition and method will now be described with reference to the following examples that will provide a better understanding of the present composition and method.

Example 1

A gelatin capsule containing 300 mg myricetin, 195 mg hesperitin and 5 mg piperine is administered orally to a patient twice a day, taken with food.

Example 2

A tablet containing sodium citrate, 500 mg myricetin, 300 mg hesperitin and 10 mg is administered orally once a day upon rising.

Example 3

A powder containing 600 mg myricetin, 390 mg hesperitin and 10 mg piperine is sprinkled onto foods such as, for example scrambled eggs after cooking but prior to consumption.

Example 4

A composition containing a blend of 55% by weight myricetin, 35% by weight hesperitin and 10% by weight piperine is blended into a saline solution and is injected intravenously, such that there is 1 mg of the composition per 1 g of saline solution.

Experimental Goal of Studies 1-4
Goal:
To determine the effectiveness of "flavonoid compounds" in limiting the replication of SARS-CoV-2.
Brief Summary of Work:
Vero E6 cells will be treated with various concentrations of four compounds sent by GlobalIRDG to PSU. Treated and untreated cells will then be infected with a predetermined concentration of SARS-CoV-2 USA/WA1-2020 strain. These cells will be monitored for survival/health for up to 72 hours post-infection.

Modification: Change in maximum concentrations of the compounds to be tested.

Specific Experiments:

A. Determination of Efficacy of Compounds Against SARS-CoV-2:
1. Vero E6 cells will be grown to a density of 105 cells per well in 24 well plate.
2. Cells will be treated with four compounds at concentrations ranging from 0 μg/ml concentration to a maximum concentration of 100 μg/ml concentration for solid powder compound and maximum dilution of 1/1000 to 1/20000 of liquid compound with three wells per each concentration for 2 hours before infection.
3. Cells will be infected with SARS-CoV-2 (USA/WA1-2020) at a viral concentration of $5 \times 10^3$ TCID50.
4. Health of cells will be monitored by light microscopy every 24 hours for 72 hours post infection. Specifically look of cytopathic effects, rounding of cells, sloughing of cells from the bottom of wells.
5. Cell death will be measured by LDH release assay at 72 hours post-infection.

Studies

The present composition and method will now be described with reference to the following studies.

The following studies were conducted to demonstrate efficacy of Equivir against coronavirus:

Study #1

Objective:

To determine the effect of Equivir against SARS-CoV-2 in Vero E6 cells.

Figure 3:
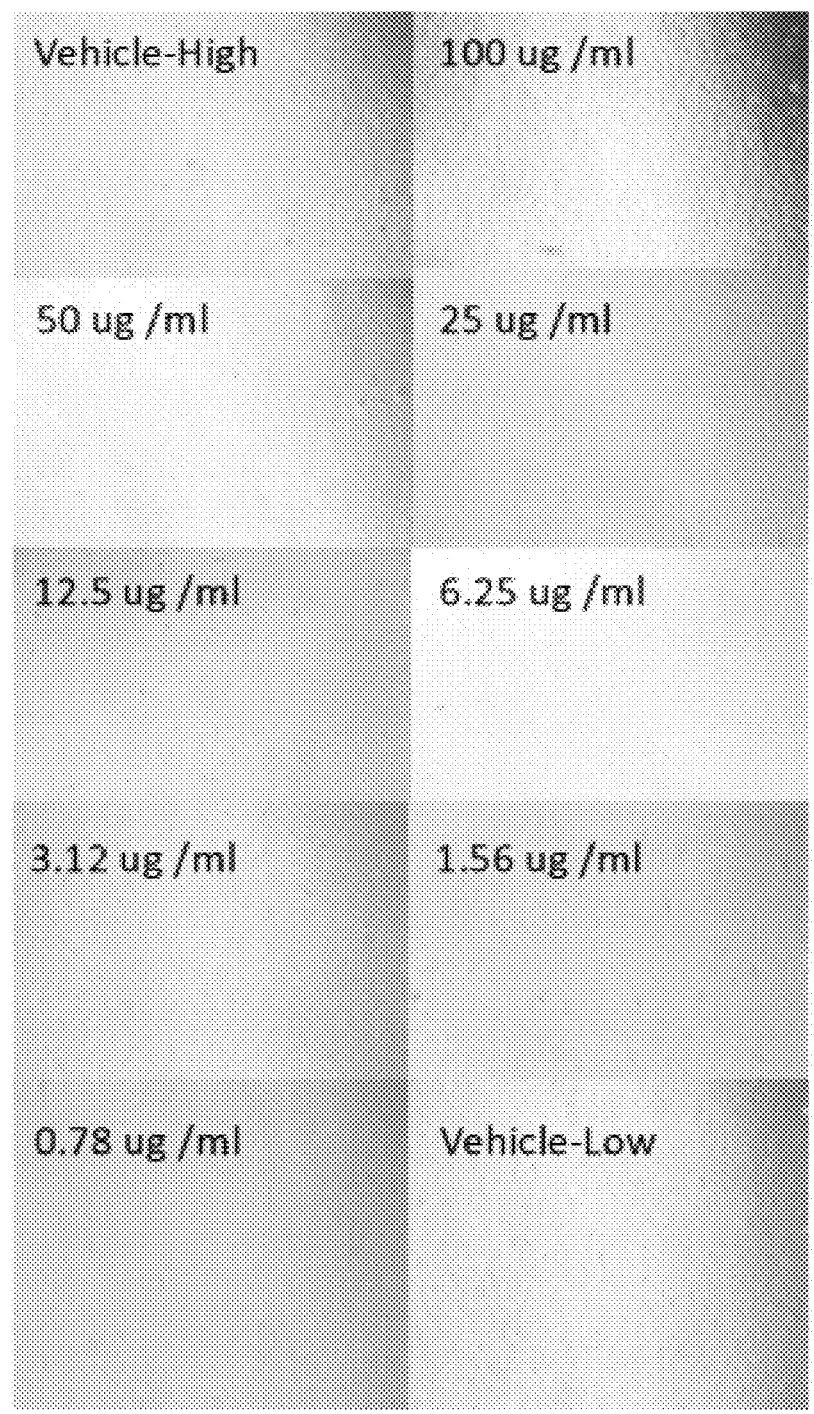
FIG. 3 illustrates the effect Equivir has on SARS-CoV-2 at various Equivir concentrations at Day 1.
Figure 4:
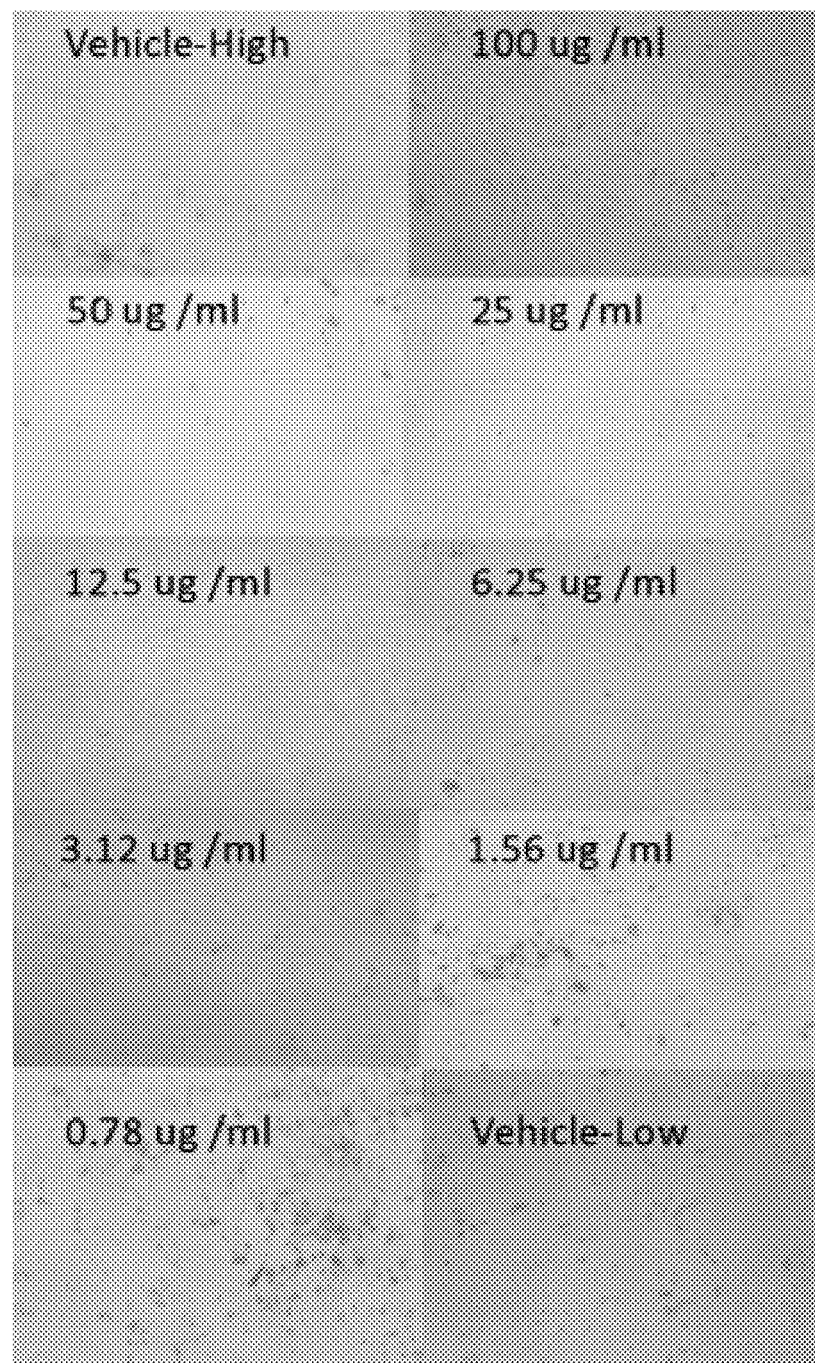
FIG. 4 illustrates the effect Equivir has on SARS-CoV-2 at various Equivir concentrations at Day 2.
Figure 5:
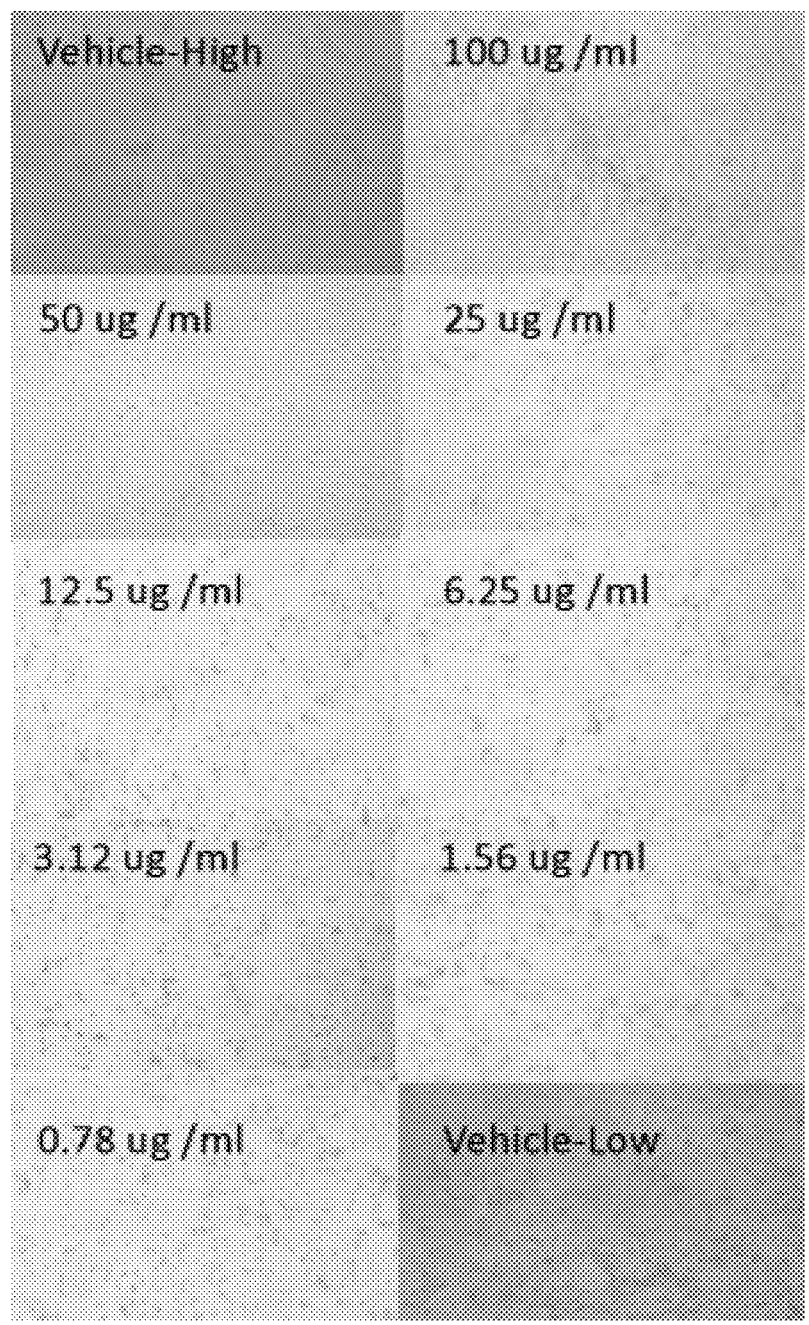
FIG. 5 illustrates the effect Equivir has on SARS-CoV-2 at various Equivir concentrations at Day 3.

Experimental Overview:

Vero E6 cells were seeded at a density of $1.5 \times 10^5$ cells/well in 24-well plates. Eight dilutions of each provided compound (Equivir, myricetin and hesperitin) and vehicle treatment (DMSO) were added simultaneously with SARS-CoV-2 (MOI. 0.03). Each concentration was tested in triplicate wells. Wells were imaged daily, and an LDH cytotoxicity assay was completed on the final day of the experiment (D3). FIGS. 3-5 are photographs representative of each concentrations on days 1-3, and are below. Representative protocol is shown below in Study 2.

Concentrations of Equivir Tested:

Equivir (μg/ml): 100, 50, 25, 12.5, 6.25, 3.125, 1.5625 and 0.78125.

Representative Protocol for Testing Equivir:

Protocol for Testing Compound LB-1

Day 1

Compound Stock Solution Preparation (Inside the BSC in MSC).

Weigh 20 mg of the compound and resuspend it in 1 ml of DMSO (cell culture grade).
Vortex well and make 10 aliquots of 100 μl. Label and store them at −20° C.

Seeding of Cells (Day before infection) (Inside BSC in Pell)

Resuspend Vero E6 cells to a final concentration of $1.5 \times 10^5$ cell/ml in MEM+10% FBS with 1× Penn/Strep.

Add 1 ml of cell suspension to each well in a 24-well plate.
Place them in $CO_2$ incubator at 37° C. O/N.

Day 0

Compound Working Solution Preparation (Inside the BSC in MSC).

Prepare MEM with 2% serum plus IX Pen/Strep.
Prepare one 10 ml sterile tube with 9.9 ml of medium. Label the tube as #1.
Prepare seven 10 ml sterile tubes with 5 ml of medium. Label the tubes as #2 to #8.
Thaw one of the tubes containing stock solution of the compound.
Add 100 μl stock solution to tube #1. Vortex well.
Transfer 5 ml from tube #1 to tube #2. Vortex well and repeat till tube #8.
Store the tubes on ice for transport to Pell.

Infection and Treatment (Inside the BSC in Pell).

Virus Preparation

Prepare Virus (SARS-CoV-2, WA1/USA-2020)
Virus Stock Concentration: $1 \times 10^{6.25}$ TCID50
Target infection MOI: 0.05 MOI
Resuspend 0.5 ml virus stock in 50 ml of MEM with 2% serum and 1× Pen/Strep (to a final concentration of $1 \times 10^{4.25}$ TCID50/ml.

Cell Preparation (Inside the BSC in Pell)

Observe under microscope and take a picture in Class IIA BSC
Transfer plates to Class IIB BSC
Remove O/M medium from the 24-well plates by suction
Add 0.5 ml virus suspension to each well (to all wells)
Add 0.5 ml of compound at each concentration to three wells from Tubes #1 to #8
Final concentration of Equivir table:

TABLE 1

| | | | | | |
|---|---|---|---|---|---|
| 100 μg/ml | 100 μg/ml | 100 μg/ml | 6.25 μg/ml | 6.25 μg/ml | 6.25 μg/ml |
| 50 μg/ml | 50 μg/ml | 50 μg/ml | 3.125 μg/ml | 3.125 μg/ml | 3.125 μg/ml |
| 25 μg/ml | 25 μg/ml | 25 μg/ml | 1.5625 μg/ml | 1.5625 μg/ml | 1.5626 μg/ml |
| 12.5 μg/ml | 12.5 μg/ml | 12.5 μg/ml | 0.78125 μg/ml | 0.78125 μg/ml | 0.78125 μg/ml |

Mix media in the wells by gently swirling the plates.
Transfer plates to incubator.

Day 1

Remove plate from incubator.
Observe cells under microscope in Class IIA BSC
Take a picture of cells at each concentration.
Transfer plates to incubator.

Day 2

Remove plate from incubator.
Observe cells under microscope in Class IIA BSC
Take a picture of cells at each concentration.
Transfer plates to incubator.

Day 3

Remove plate from incubator.
Observe cells under microscope in Class IIA BSC
Take a picture of cells at each concentration.
Transfer plate to Class IIB BSC
Remove 0.5 ml from each well and transfer to 1 ml eppendorff tubes. Label the tubes.
Set up centrifuge tubes in Class IIB BSC.
Centrifuge tubes at 5,000 g for 5 min.
Transfer 100 μl from each tube to 96 well-plate
Perform LDH release assay as per the instruction of the kit.

Summary of Results:

Effectiveness of compounds against SARS-CoV-2 were tested by treating Vero E6 cells with various compounds added at the time of infection with a MOI of 0.03. Equivir showed no toxicity at tested concentrations and was effective in inhibiting viral replication at higher concentrations (100 and 50 g/ml).

TABLE 2

Effectiveness of Equivir at different concentrations

| | 100 µg/ml | 50 µg/ml | 25 µg/ml | 12.5 µg/ml | 6.25 µg/ml | 3.125 µg/ml | 1.5625 µg/ml | 0.78125 µg/ml |
|---|---|---|---|---|---|---|---|---|
| Equivir | Effective | Effective | Effective | Not Effective | Not Effective | Not Effective | Not Effective | Not Effective |

Figure 6:
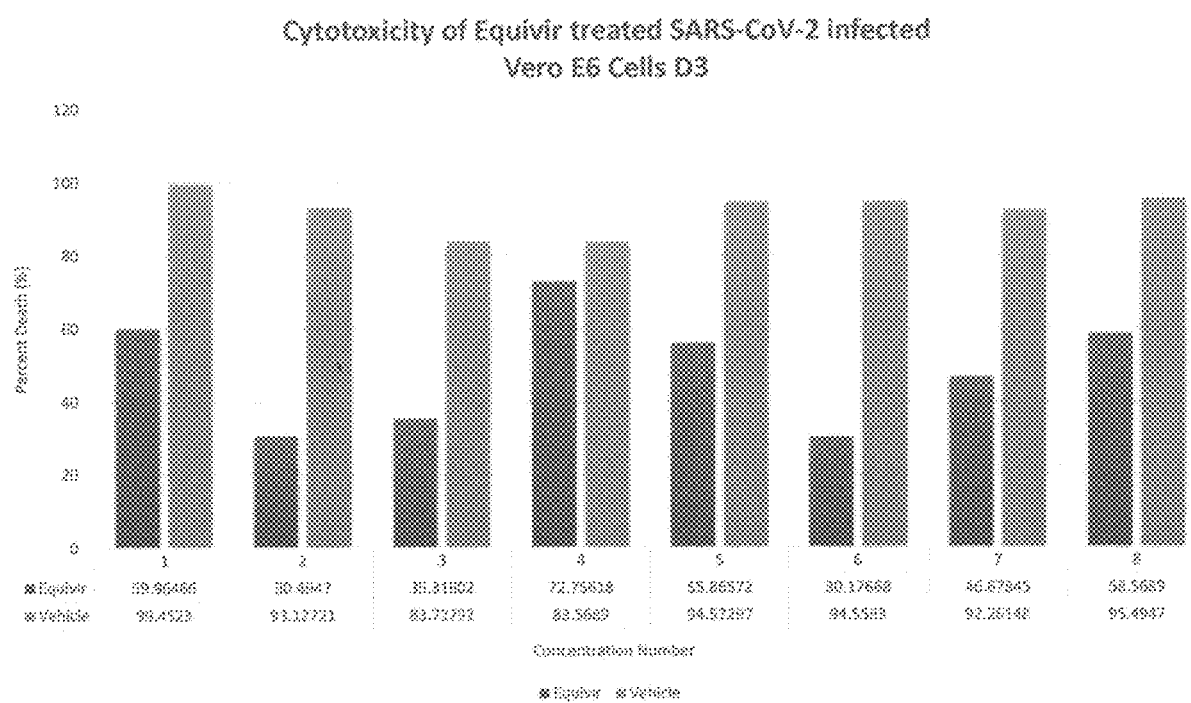
FIG. 6 is a graph showing cytotoxicity of Equivir treated SARS-CoV-2.

FIG. 6 is a graph that shows that Equivir is not toxic.

Study #2

Objective:

To determine the effect of Equivir against SARS-CoV-2 in Vero E6 cells.

Experimental Overview:

Vero E6 cells were seeded at a density of $5 \times 10^4$ cells/well in 96-well plates. Eight dilutions of Equivir and vehicle treatment (DMSO) were added simultaneously with SARS-CoV-2 (MOI: 0.01). Each concentration was tested in triplicate wells. Wells were imaged daily, and an LDH cytotoxicity assay was completed on the final day of the experiment (D3). Representative images of each concentrations on day 3 are below.

Concentrations of Equivir Tested:

Equivir (µg/ml): 1000, 500, 250, 125, 62.5, 31.25, 15.625 and 7.8125.

Summary of Results:

Effectiveness of compounds against SARS-CoV-2 were tested by treating Vero E6 cells with various compounds added at the time of infection with a MOI of 0.01. Equivir was toxic at higher concentrations and not toxic at lower concentrations. Equivir was effective in inhibiting viral replication at non-toxic concentrations of 250, 125, and 62.5 µg/ml.

TABLE 3

| Baseline concentration | 25 µg/ml | 12.5 µg/ml | 6.25 µg/ml | 3.125 µg/ml | 1.5625 µg/ml | 0.78125 µg/ml | 0.39 µg/ml | 0.19 µg/ml |
|---|---|---|---|---|---|---|---|---|
| Equivir Concentration | 1000 µg/ml | 500 µg/ml | 250 µg/ml | 125 µg/ml | 62.5 µg/ml | 31.25 µg/ml | 15.625 µg/ml | 7.8125 µg/ml |
| Equivir effect | Toxic | Toxic | Effective | Effective | Effective | Not Effective | Not Effective | Not Effective |

Figure 7:
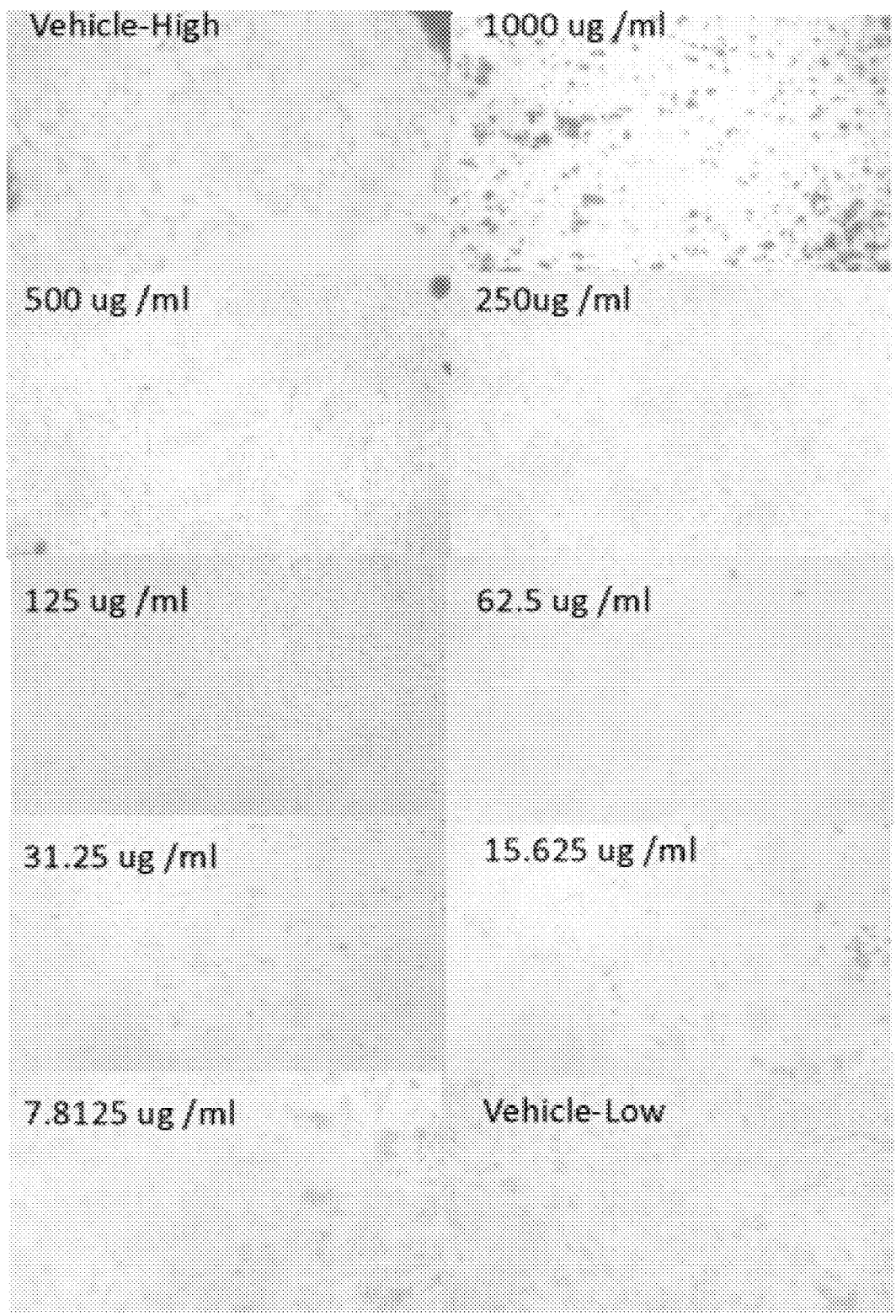
FIG. 7 illustrates effectiveness of various concentrations of Equivir against SARS-CoV-2.

FIG. 7 are photographs showing efficacy.

FIG. 8 is a graph showing cytotoxicity.

Study #3

Objective:

To determine the prophylactic and post-infection efficacy of Equivir treatment against SARS-CoV-2 in Vero E6 cells.

Experimental Overview:

Vero E6 cells were seeded at a density of $1.5 \times 10^5$ cells/well in 24-well plates. Four different concentrations of Equivir were added either 2 hours prior to or after infection with SARS-CoV-2 (MOI. 0.01). Each concentration was tested in triplicate wells. Wells were imaged daily, and an LDH cytotoxicity assay was completed on the final day of the experiment (D3). Representative images of each concentrations on day 3 are below.

Concentrations of Various Compounds Tested:

Equivir (µg/ml): 200, 100, 50, and 25.

These concentrations were chosen since no toxicity was observed at these concentrations and was effective when the virus and compound were added at the same time.

Figure 9:
FIG. 9 shows the effectiveness of various concentrations of Equivir at less than 2 hours for various Equivir concentrations.
Figure 10:
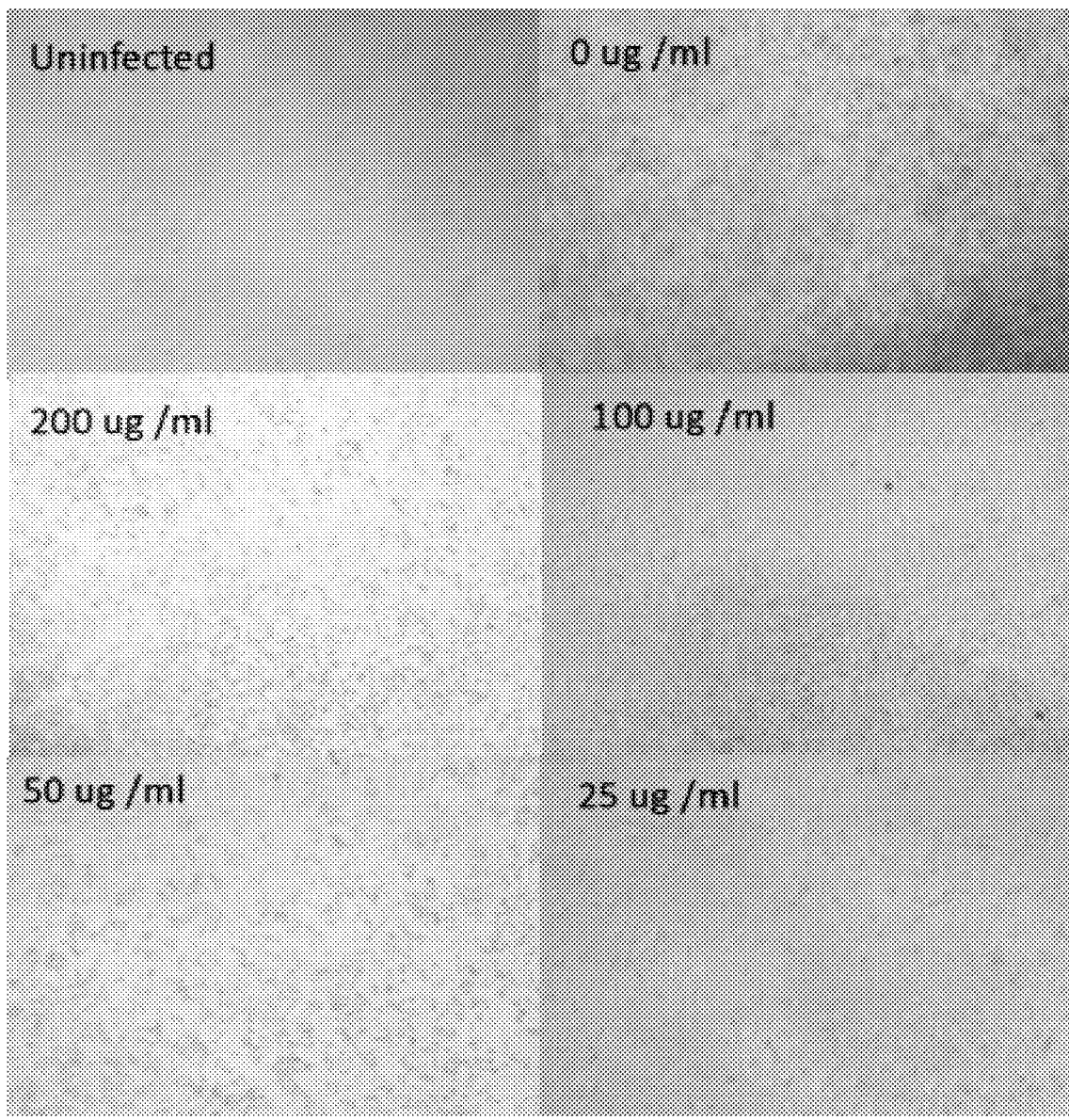
FIG. 10 illustrates effectiveness of various concentrations of Equivir at various concentrations for over 2 hours.

Summary of the Results:

Referring to FIGS. 9-11, effectiveness of Equivir against SARS-CoV-2 were tested by treating Vero E6 cells with various compounds added before and after infection with a MOI of 0.01. Equivir was not toxic at tested concentrations. Equivir was effective in inhibiting viral replication at non-toxic concentrations of 200 and 100 µg/ml.

TABLE 4

| | 200 µg/ml | 100 µg/ml | 50 µg/ml | 25 µg/ml |
|---|---|---|---|---|
| Effectiveness of Equivir at Various Concentrations | Effective | Effective | Not Effective | Not Effective |
| Equivir | Effective | Effective | Not Effective | Not Effective |

Study #4

Overall Summary of Studies:

Equivir is not toxic to Vero E6 cells below 250 µg/ml concentration.

Equivir is effective in inhibiting SARS-CoV-2 at a MOI of 0.01 in Vero E6 cells at doses ranging from 50 to 250 µg/ml when the virus and drug is added at the same time.

Equivir is effective in inhibiting SARS-CoV-2 at a MOI of 0.01 in Vero E6 cells at doses ranging from 100 to 200 μg/ml when the drug is added either 2 hours before or after the virus.

Experimental Goal of Studies 5-9

Goal:

To determine the efficacy of Equivir against SARS-CoV-2.

Brief Summary of Work:

Calu-3 (human lung adenocarcinoma cell line) cells infected with SARS-CoV-2 (WA1/USA-2020) will be treated with various concentrations of Equivir and the effectiveness of the drug will be determined by TCID50, qRT-PCR, and NP protein immunohistochemistry.

Specific Experiments:
A. Determination of Effectiveness of Equivir Against SARS-CoV-2:
1. Calu-3 cells will be grown in 24-well plate.
2. Cells will be infected with SARS-CoV-2 (WA1/USA-2020) at 0.05 MOI.
3. Cells will be treated with Equivir at concentrations of 25, 50, 100, 150, and 200 μg/ml at −2, 0, and +2 hours post-infection.
4. Health of cells will be monitored for 72 hours.
5. Supernatants from three wells will be used for estimation of viral growth by TCID50 assay at 48 hours under all conditions (four Equivir concentrations and three treatment periods).
6. Supernatants from three wells will be used for estimation of viral growth by qRT-PCR assay at 72 hours under all conditions (four Equivir concentrations and three treatment periods).
7. Three wells of Infected cells (at 48 hours post-infection with four different concentration of Equivir and three treatment conditions) will be fixed and stained with fluorescent labelled anti-NP antibody and imaged using fluorescent microscope.
8. The data from each assay will be compared with infected but not treated and treated but not infected cells.
9. Cell death will be measured by LDH release assay at 48-hour post-infection in all conditions.

B. Determination of Effectiveness of Equivir Against SARS-CoV-2:
10. Calu-3 cells will be grown in 24-well plate.
11. Cells will be infected with SARS-CoV-2 (WA1/USA-2020) at 0.05 MOI.
12. Cells will be treated with Equivir at concentrations of 50, 100, 200, and 250 μg/ml with 10% W/v gallic acid at −2, 0, and +2 hours post-infection.
13. Health of cells will be monitored for 72 hours.
14. Supernatants from three wells will be used for estimation of viral growth by TCID50 assay at 48 hours under all conditions (four Equivir concentrations and three treatment periods).
15. Supernatants from three wells will be used for estimation of viral growth by qRT-PCR assay at 48 hours under all conditions (four Equivir concentrations and three treatment periods).
16. Three wells of Infected cells (at 48 hours post-infection with four different concentration of Equivir and three treatment conditions) will be fixed and stained with fluorescent labelled anti-NP antibody and imaged using fluorescent microscope.
17. The data from each assay will be compared with infected but not treated and treated but not infected cells.

Deliverables:
1) TCID50 values at 48 hours following infection and treatment with Equivir.
2) Viral titers by q-RT-PCRT at 72 hours following infection and treatment with Equivir.
3) At least 3 images (40×) of fluorescent ant-NP staining of cells under each condition along with appropriate controls.

SARS-CoV-2 Infection Assay/TCID$_{50}$ General Protocol—MJN—Adapted from Sutton Lab:
1. Prepare stock solution at 20 mg/mL in DMSO. Aliquot and store at −20° C.
2. Seed designated cell type in either 24- or 96-well plate 24 hr prior to infection. Place in CO$_2$ incubator at 37 C.
3. On day of infection, prepare compound working solutions to specified concentrations and dilute viral stock for targeted MOI.
4. Add virus suspension, treatment, or combination of the two as necessary to individual wells at either −2 hr, 0 hr, or +2 hr timepoints.
5. Incubate virus with cells for 1 hr at 37° C., and then aspirate virus suspension.
6. Replace with treatment compound or plain media, and incubate cells for predetermined time.
7. Following incubation, collect supernatant from each well and spin down to purify.
8. For 24-well TCID$_{50}$, seed plated with Vero E6 cells 24 hr prior to assay. Place in CO$_2$ incubator at 37° C.
9. Serially dilute stock concentrations at 1:10 out to $10^{-10}$.
10. Aspirate old media from Vero E6 cells and add 900 μl/well of fresh media with 2% FBS.
11. Starting with the most dilute supernatant sample ($10^{-10}$), add 100 μl of each sample to four pre-labeled Vero E6 wells. Continue adding 100 μl of each sample to corresponding wells, working from the most dilute to the most concentrated samples.
12. Make sure to have untreated wells for negative controls.
13. Incubate at 37° C. for 72 hrs before reading cytopathic effects and calculating TCID$_{50}$ values.

SARS-CoV-2 qRT-PCR Protocol—MJN:
1. Isolate RNA from cells or tissue using a previously described protocol combining TRIzol and the Invitrogen PureLink RNA Mini Kit.
2. Confirm viral inactivation of samples via previously described protocols before taking processed RNA samples to BSL2 facility.
3. Nanodrop RNA samples for quality check and concentration values.
4. Normalize RNA concentrations across samples.
5. Generate cDNA with BioRad iScript cDNA Kit and dilute final product at 1:20 in RNase free water.
6. Perform qPCR for SARS-CoV-2 N2 protein using BioRad CFX Connect system. Add 5 μl of diluted cDNA of each sample to respective volumes of BioRad SsoAdvanced Universal SYBR Green SuperMix, IDT nCOV_N2 (SUN) Probe, and water. Include pre-calculated positive control samples.

Obtain quantification or threshold cycle value through CFX Manager™ Software, and calculate gene copy number based on the standard.

SARS-CoV-2 IFA Assay Protocol—MJN—Adapted from Jose Lab:
1. Seed cells in 24-well plates with glass coverslips in the bottom of each well.
2. Perform infection assay with SARS-CoV-2 and incubate for 48-72 hrs.
3. Gently wash the infected cells with phosphate-buffered saline (PBS) three times before fixing.
4. Fix the cells using 3.7% paraformaldehyde (500 ul/well) in PBS for 30 min at room temperature.
5. Wash 3× in PBS (1 ml/well).
6. Permeabilize the cells using 0.1% Triton X-100 in PBS (500 μl/well) for 15 min.
7. 250 μl of Triton X-100 to 24.75 ml of 1×PBX to make 25 ml of 25 ml of 0.1% Triton X-100.
8. Wash 3× in PBS (1 ml/well) each 3 min.
9. Confirm viral inactivation of the plate via previously described protocols before taking fixed cells to BSL2 facility.—Keep plate at 4° C.

10. Blocking: 1 hr to overnight at 4 C with PBS+10 mg/mL bovine serum albumin (500 ul/well).
11. Remove the blocking solution. Add 50 µl of Primary antibody for 1 hr (diluted in PBS+ with 10 mg/mL bovine serum. Rock on the rocker at room temperature for one hour.
12. Remove the solution, Wash 3× in PBS (500 µl/well).
13. From here, do all experiments under dark condition. Cover the plate using aluminum foil and turn off the lights in the hood. Incubate with 50 µl secondary antibody in PBS +10 mg/mL bovine serum. Rock on the rocker at room temperature for 1 hr.
14. Stain the nuclei using Hoechst stain (0.2 to 2 µg/mL) in PBS for 15 min.
15. Wash 3× in PBS (500 µl/well) each 3 min. Leave PBS on well plate.
16. Mount the cover slides onto glass slides with one drop of Fluorsave and use transparent nail polish to seal the slides.
17. Store in the dark at 4° C. until ready to image.

Figure 12:
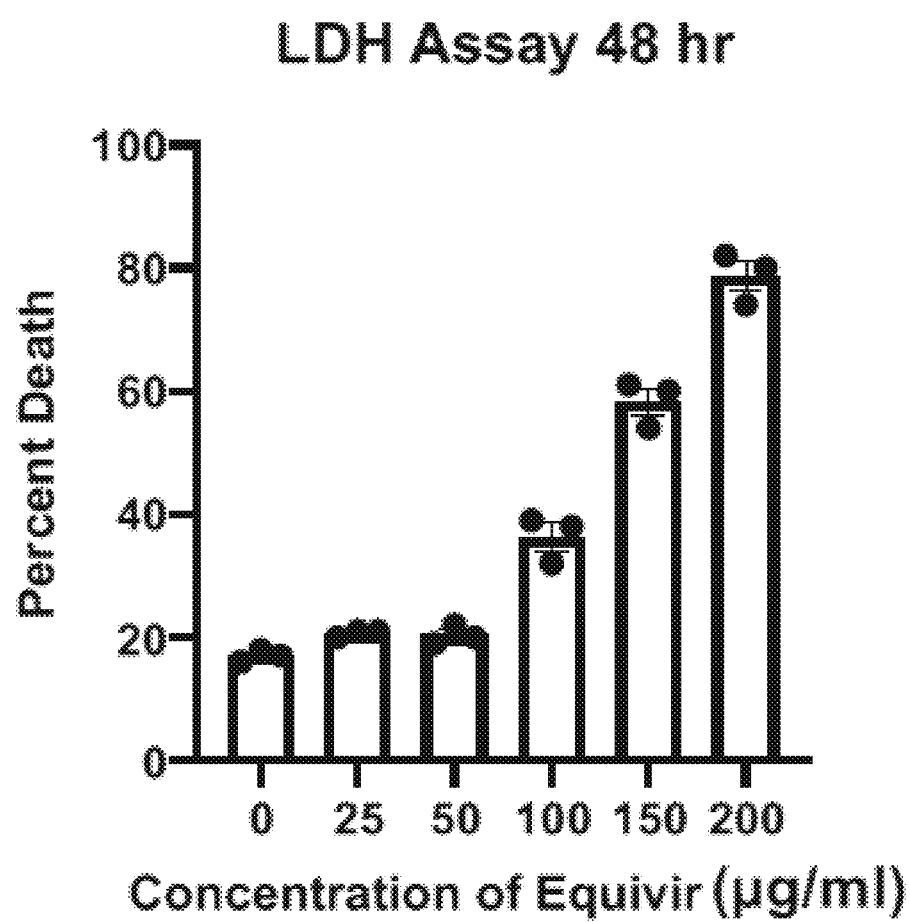
FIG. 12 is a graph showing percent cell death versus concentration of Equivir.
Figure 13:
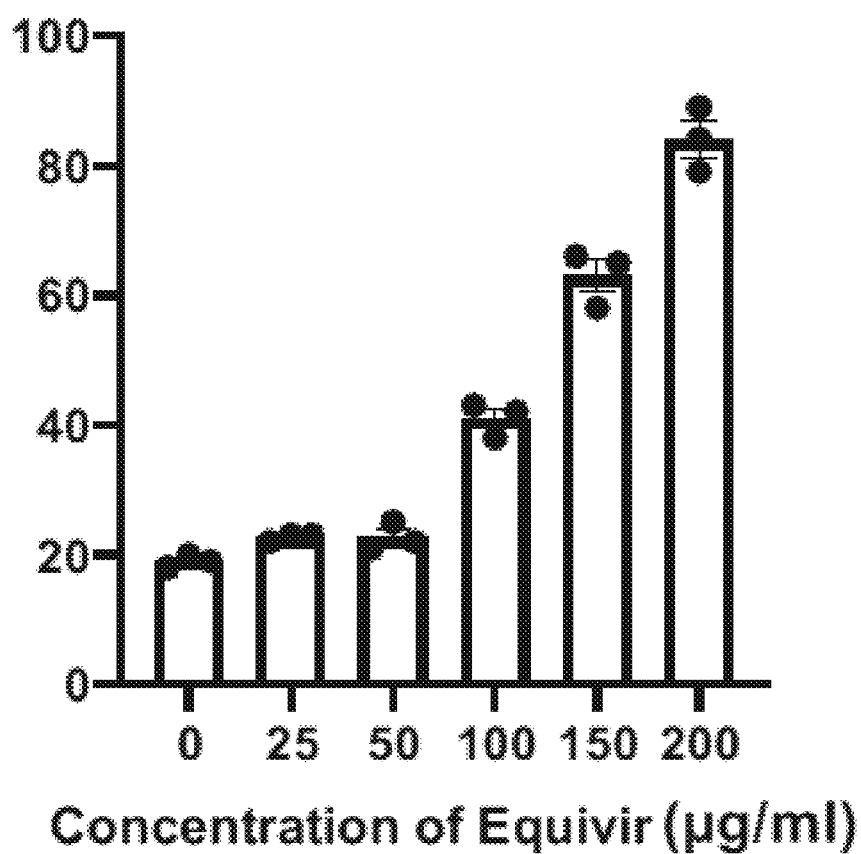
FIG. 13 is a graph showing percent cell death versus concentration of Equivir.
Figure 14A:
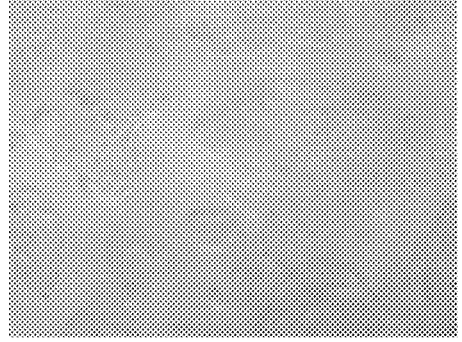
FIG. 14a is an image of Calu-3 from DO (untreated cells).
Figure 14B:
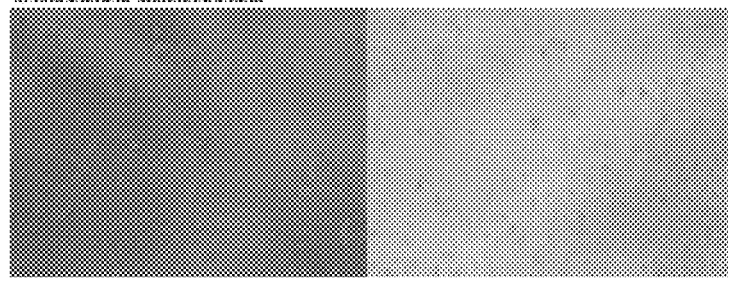
FIG. 14b is an image showing untreated/unaffected representative of Calu-3 from D2 and D3 (48 and 72 hr PI).
Figure 15A:
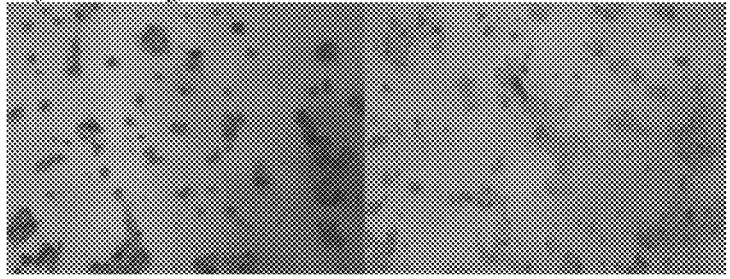
FIG. 15a are images of infected cells with Equivir 200 µg/ml.
Figure 15B:
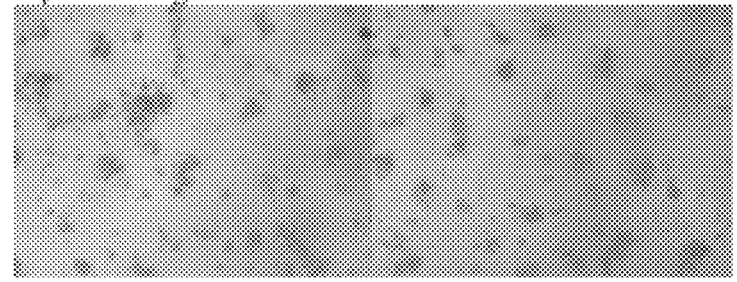
FIG. 15b are images of infected cells with Equivir 150 µg/ml.
Figure 15C:
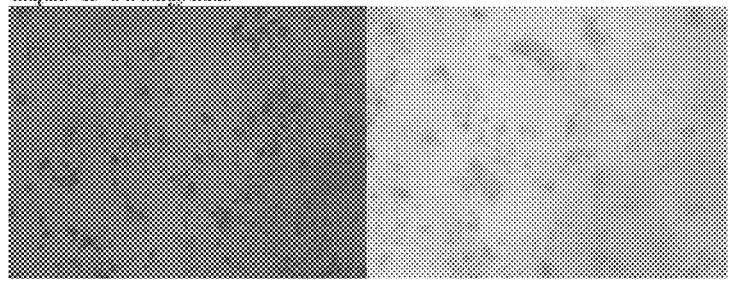
FIG. 15c are images of infected cells with Equivir 100 µg/ml.
Figure 15D:
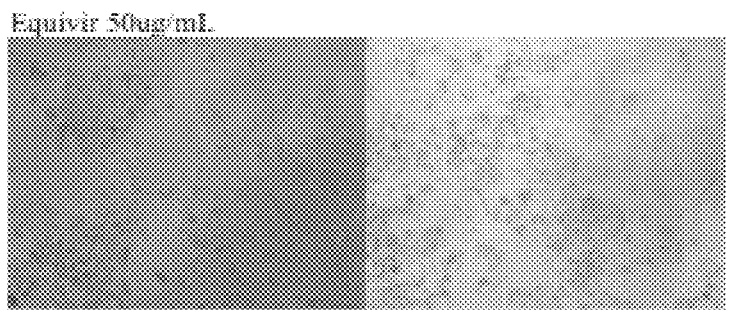
FIG. 15d are images of infected cells with Equivir 50 µg/ml.
Figure 15E:
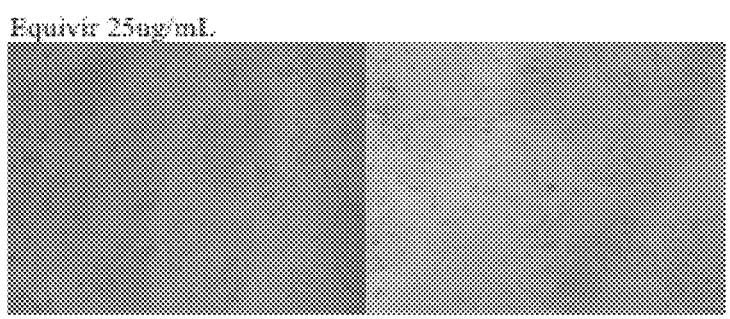
FIG. 15e are images of infected cells with Equivir 25 µg/ml.
Figure 16:
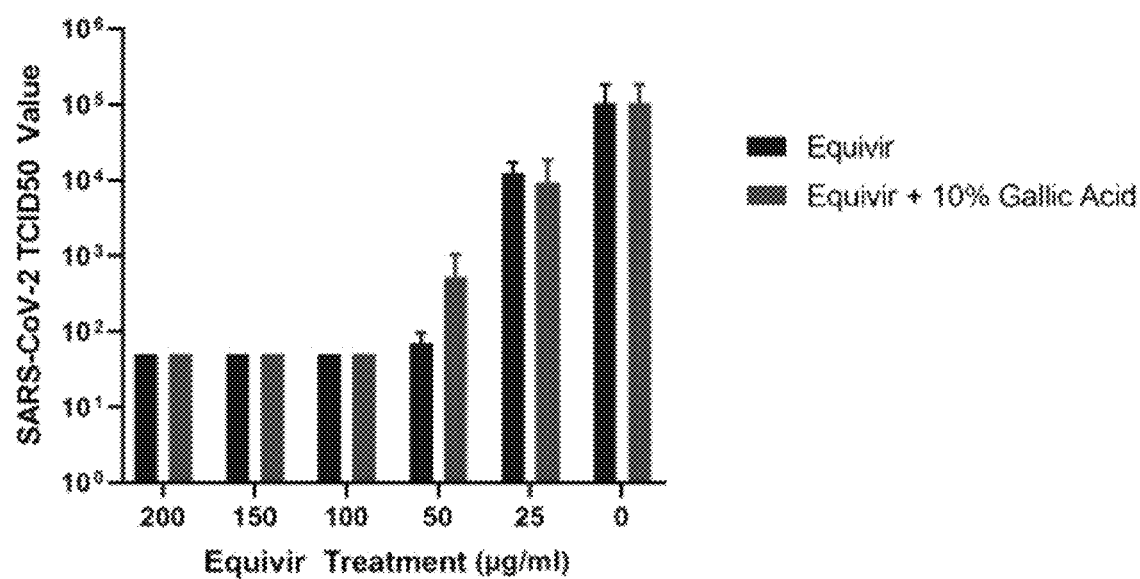
FIG. 16 is a graph of SARS-CoV-2 versus Equivir treatment.
Figure 17:
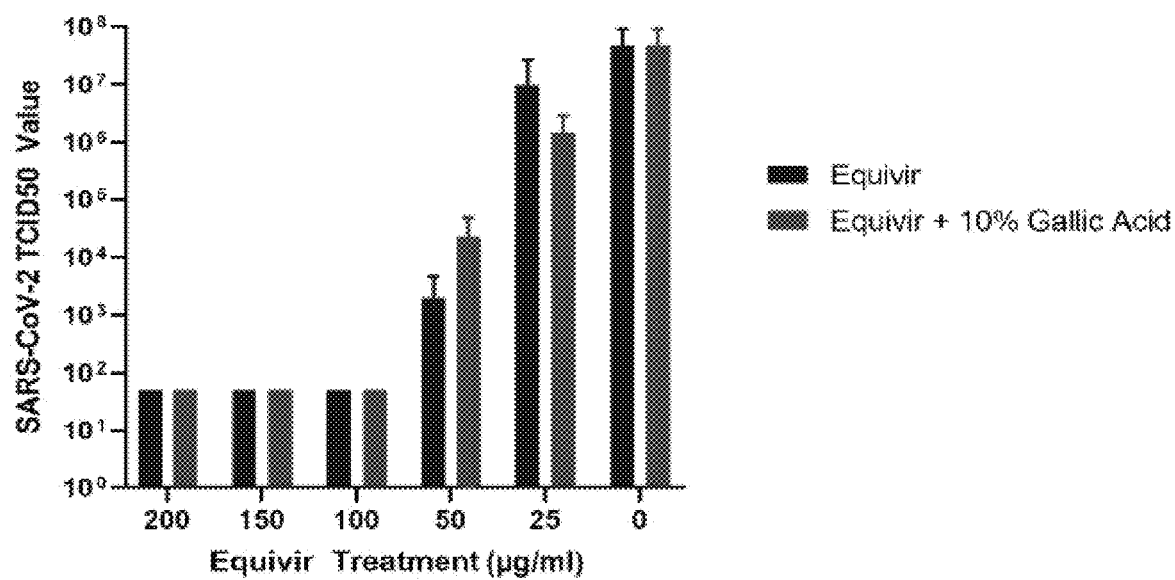
FIG. 17 is a graph showing SARS-CoV-2 versus Equivir concentration.
Figure 18A:
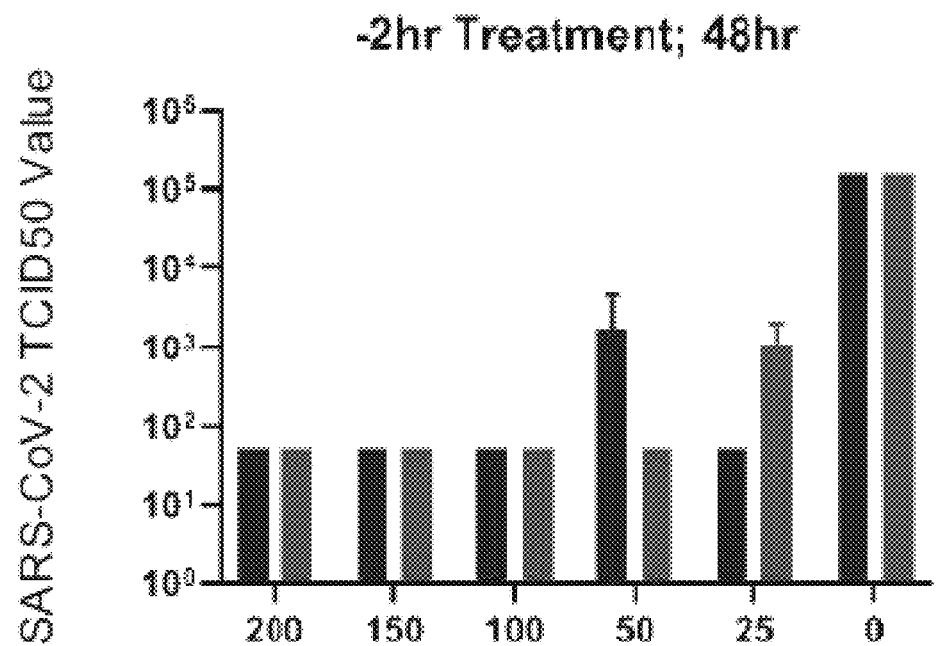
FIGS. 18a and 18b are graphs showing SARS-CoV-2 with Equivir treatment less than 2 hours at 48 hours and 72 hours, respectively.
Figure 18B:
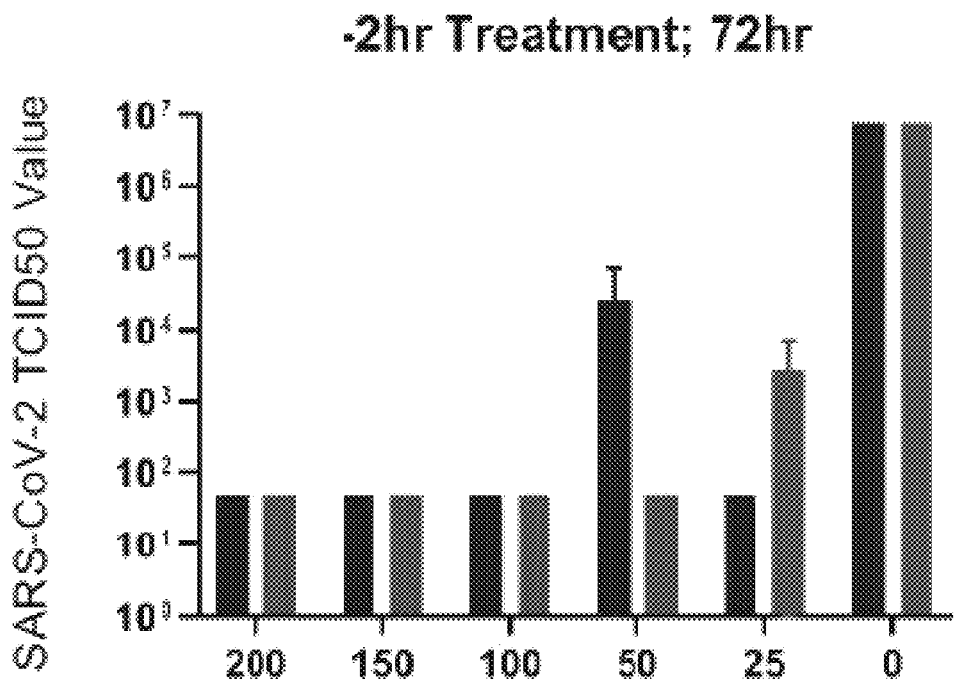
Figure 19A:
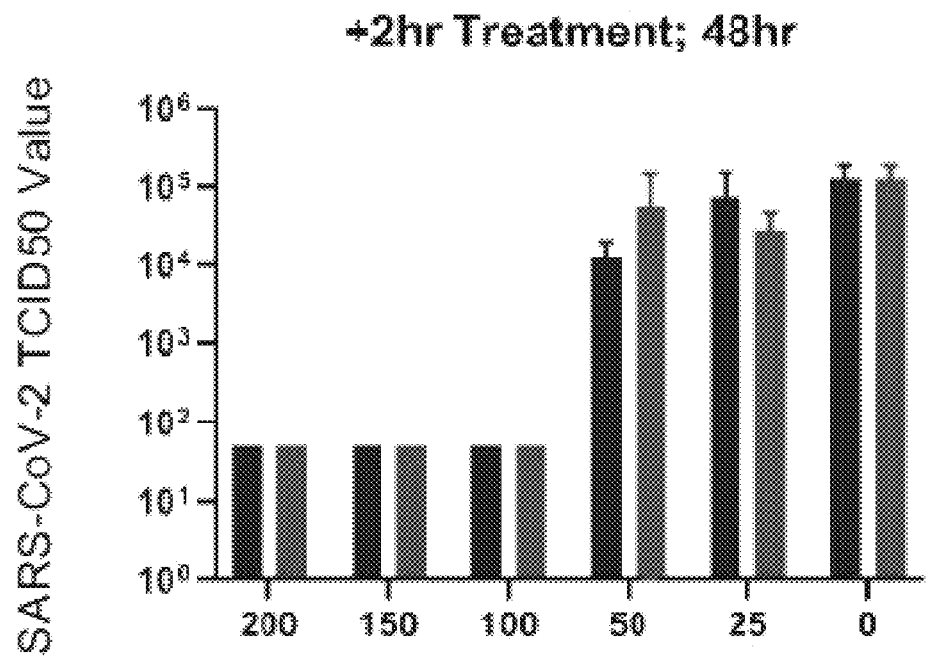
FIGS. 19a and 19b are graphs showing SARS-CoV-2 with Equivir treatment at more than 2 hours at 48 hours and 72 hours, respectively.
Figure 19B:
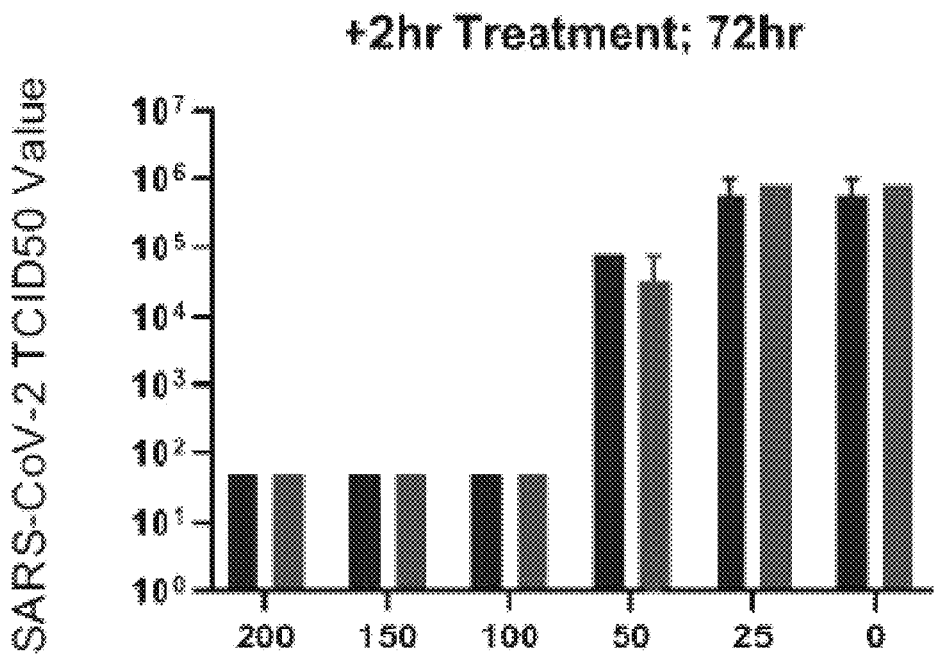
Figure 20:
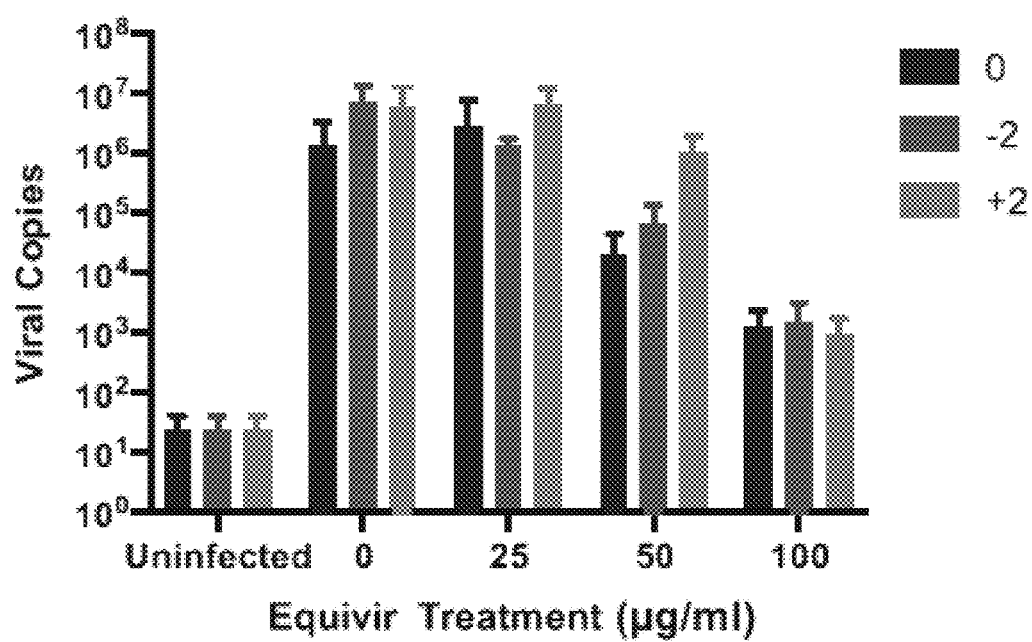
FIG. 20 is a graph showing viral copies versus Equivir.
Figure 21:
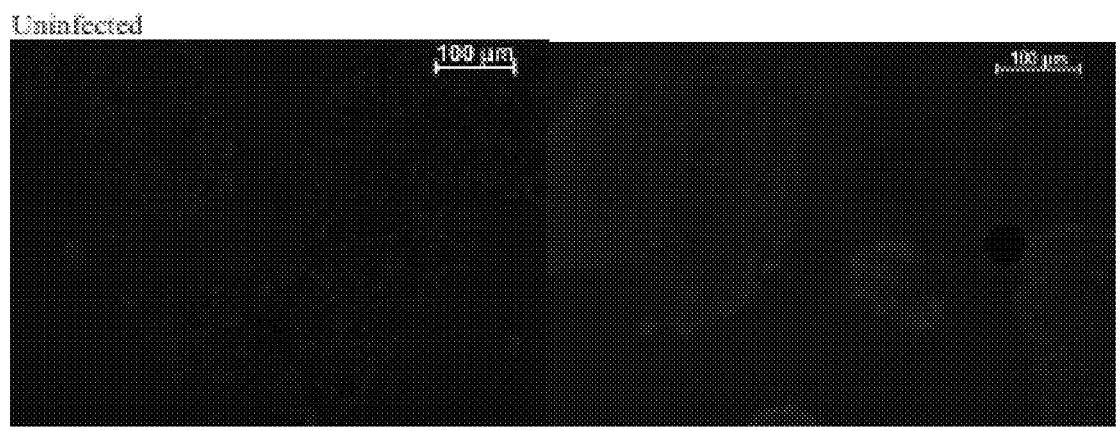
FIG. 21 is a photograph showing uninfected cells.
Figure 22:
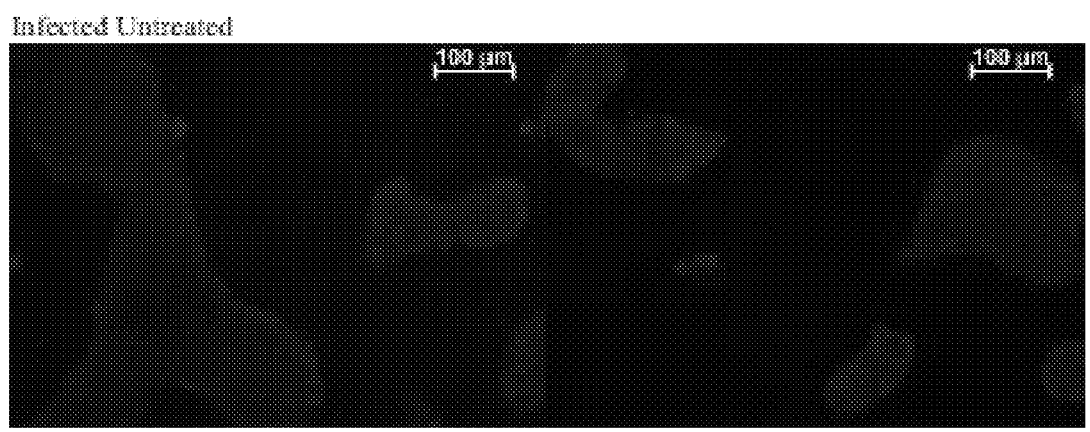
FIG. 22 is a photograph showing infected untreated cells.
Figure 23:
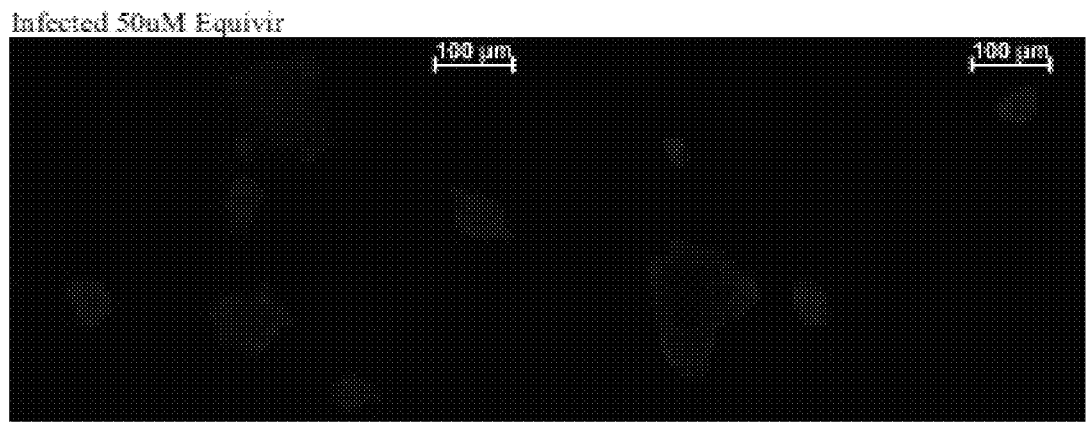
FIG. 23 is a photograph showing infected cells with 50 µM Equivir.
Figure 24:
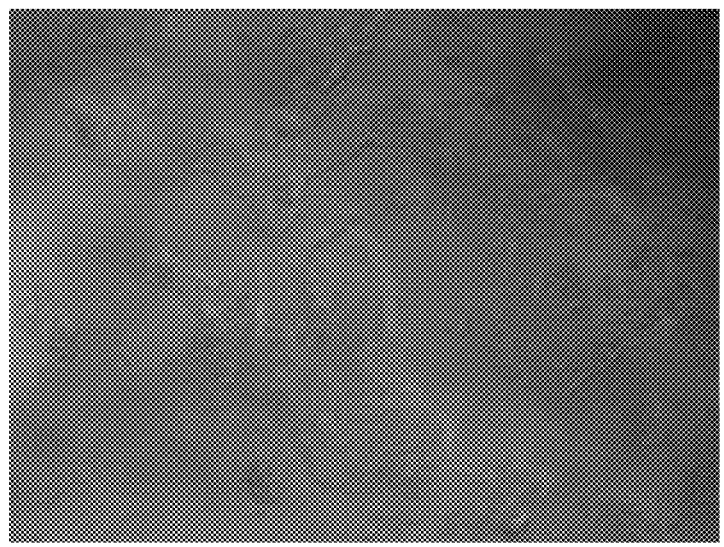
FIG. 24 is an image of Calu-3 from untreated cells.
Figure 25:
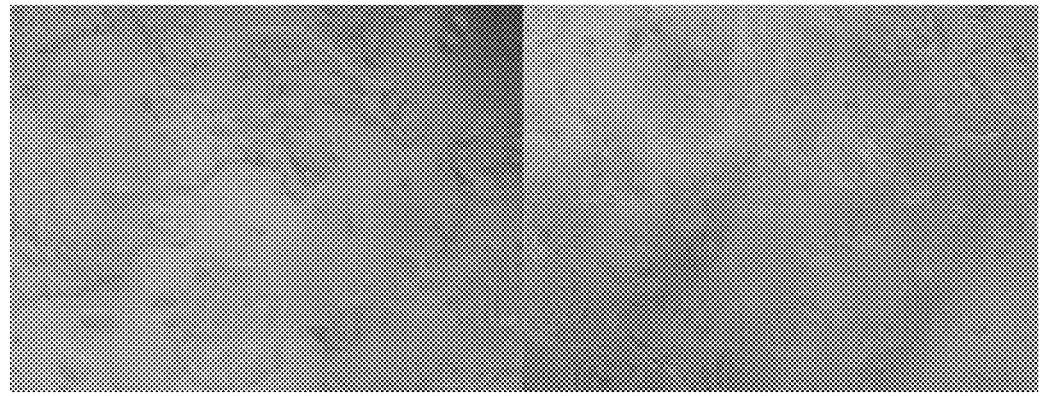
FIG. 25 are images of uninfected cells added to cells 2 hours prior to infection with SARS-CoV-2.
Figure 26:
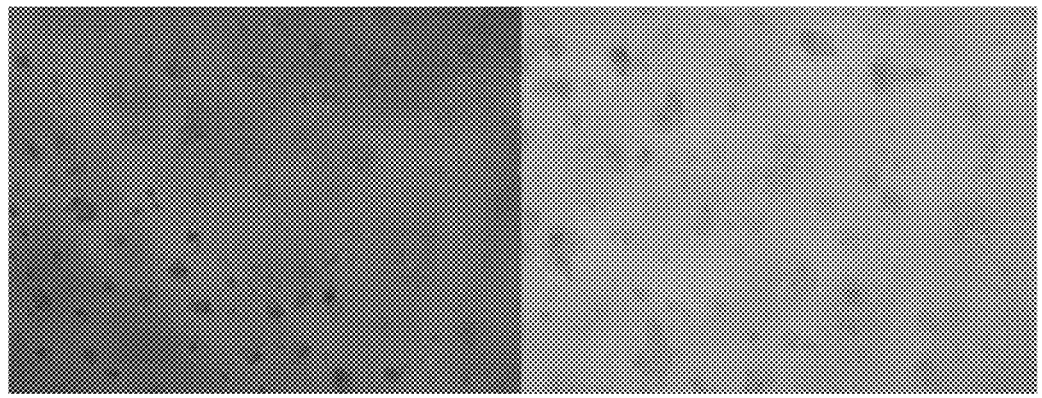
FIG. 26 are images of infected cells with Equivir at 200 µg/ml, added to cells 2 hours prior to infection with SARS-CoV-2.
Figure 27:
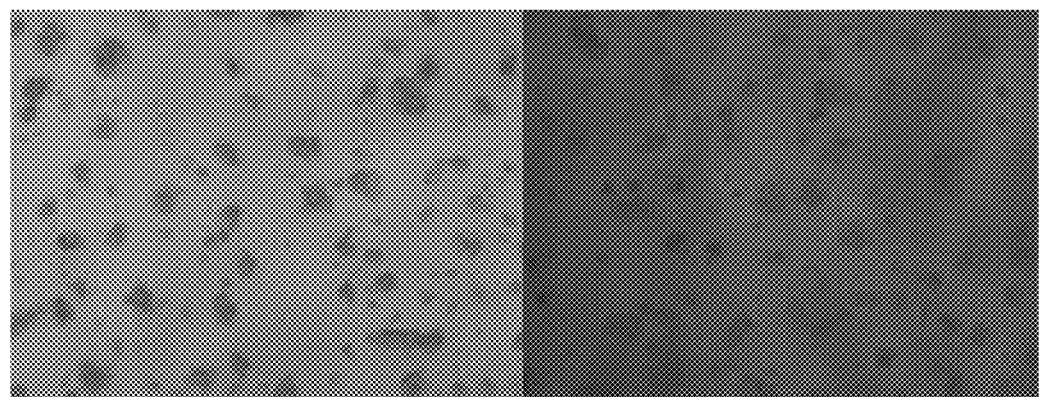
FIG. 27 are images of infected cells with Equivir at 150 µg/ml, added to cells 2 hours prior to infection with SARS-CoV-2.
Figure 28:
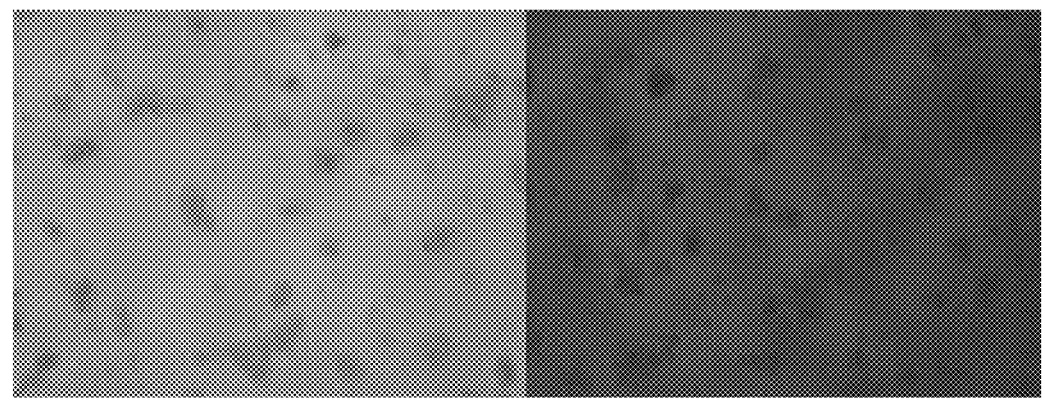
FIG. 28 are images of infected cells with Equivir at 100 µg/ml, added to cells 2 hours prior to infection with SARS-CoV-2.
Figure 29:
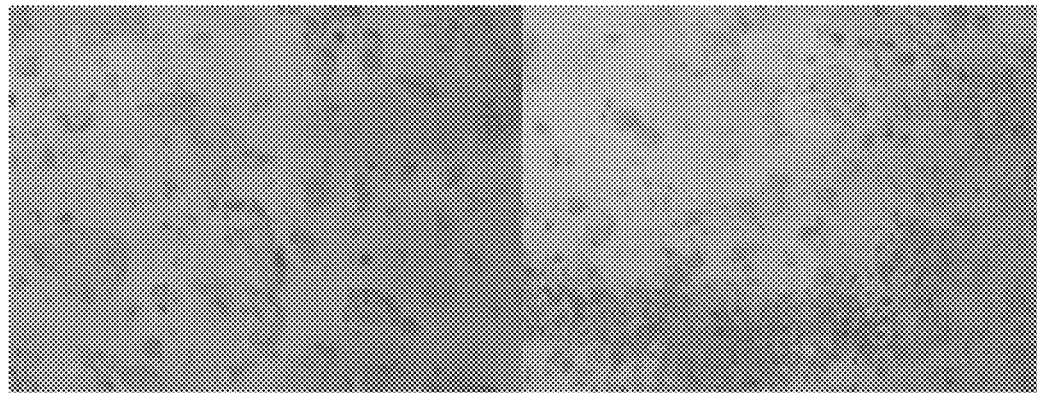
FIG. 29 are images of infected cells with Equivir at 50 μg/ml, added to cells 2 hours prior to infection with SARS-CoV-2.
Figure 30:
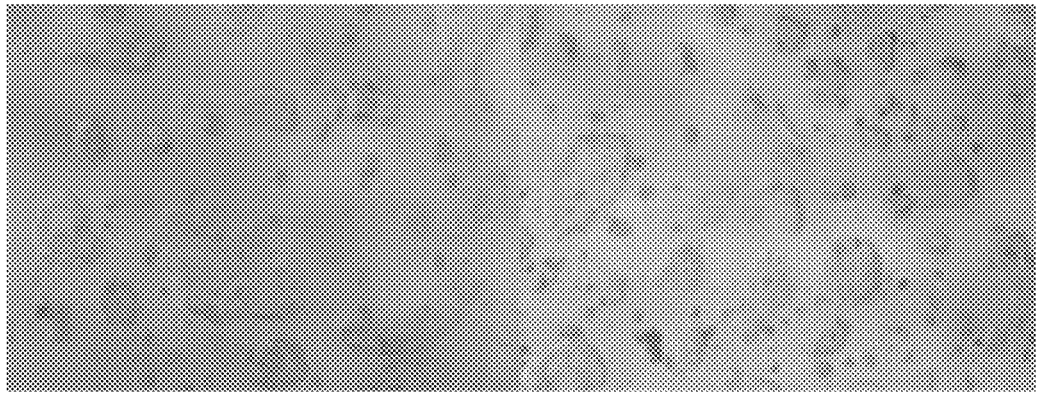
FIG. 30 are images of infected cells with Equivir at 25 μg/ml, added to cells 2 hours prior to infection with SARS-CoV-2.
Figure 31:
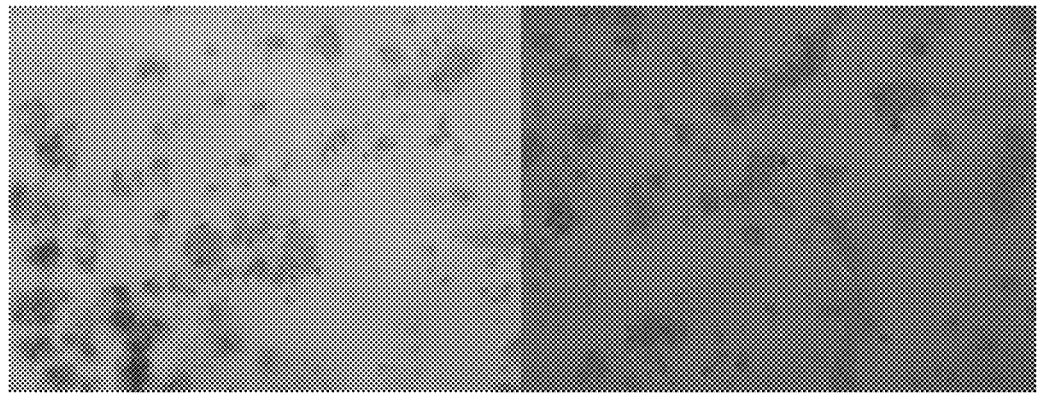
FIG. 31 are images of Equivir 200 μg/ml and gallic acid 20 μg/ml, added to cells 2 hours prior to infection with SARS-CoV-2.
Figure 32:
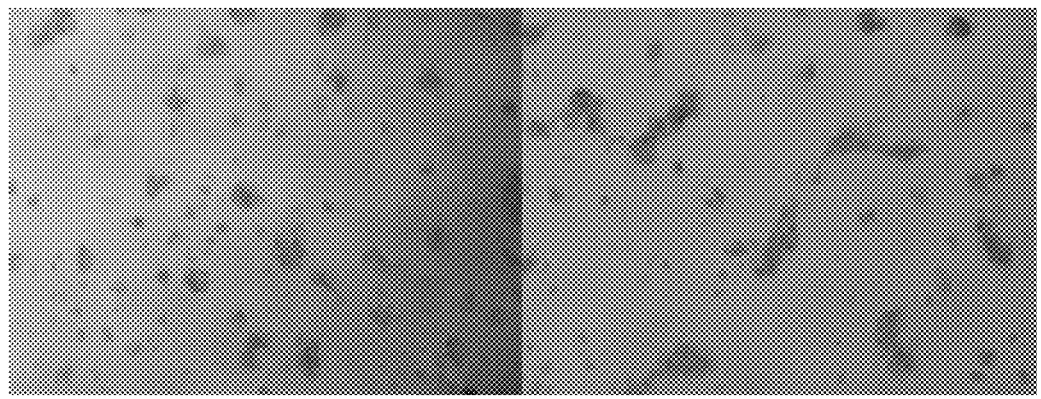
FIG. 32 are images of Equivir 150 μg/ml and gallic acid 15 μg/ml, added to cells 2 hours prior to infection with SARS-CoV-2.
Figure 33:
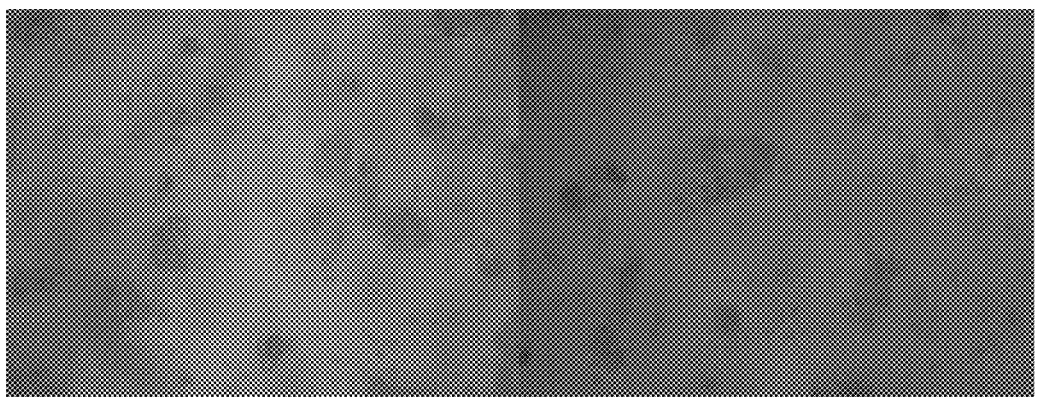
FIG. 33 are images of Equivir 100 μg/ml and gallic acid 10 μg/ml, added to cells 2 hours prior to infection with SARS-CoV-2.
Figure 34:
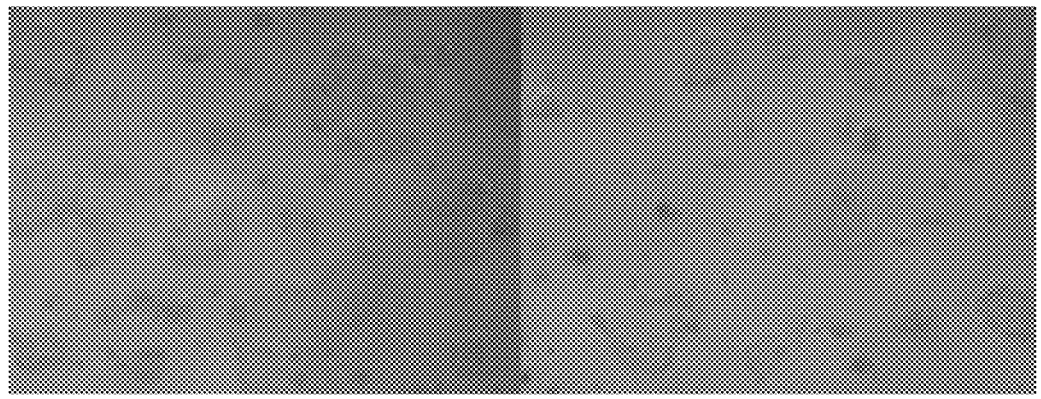
FIG. 34 are images of Equivir 50 μg/ml and gallic acid 5 μg/ml, added to cells 2 hours prior to infection with SARS-CoV-2.
Figure 35:
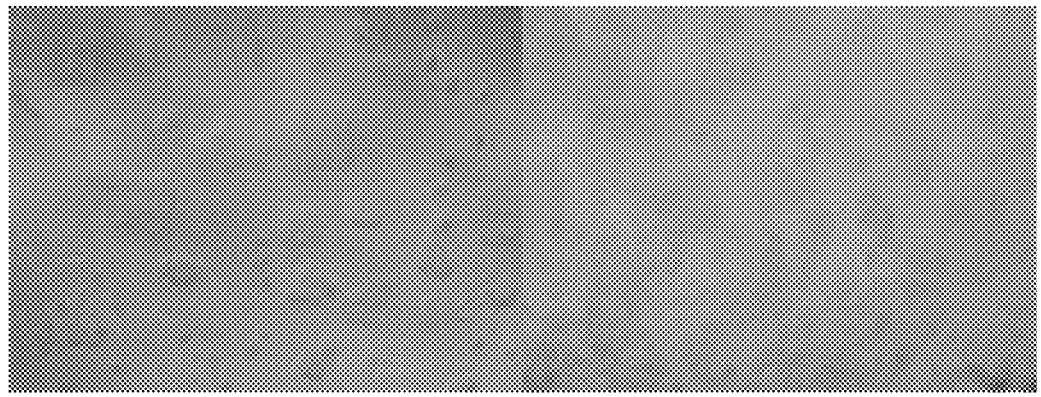
FIG. 35 are images of Equivir 25 μg/ml and gallic acid 2.5 μg/ml, added to cells 2 hours prior to infection with SARS-CoV-2.
Figure 36:
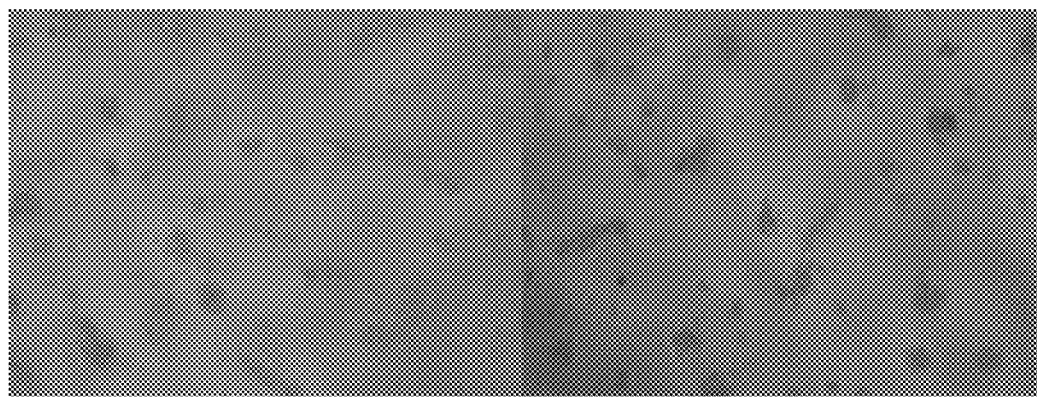
FIG. 36 are images of Equivir 200 μg/ml, added to cells 2 hours after to infection with SARS-CoV-2.
Figure 37:
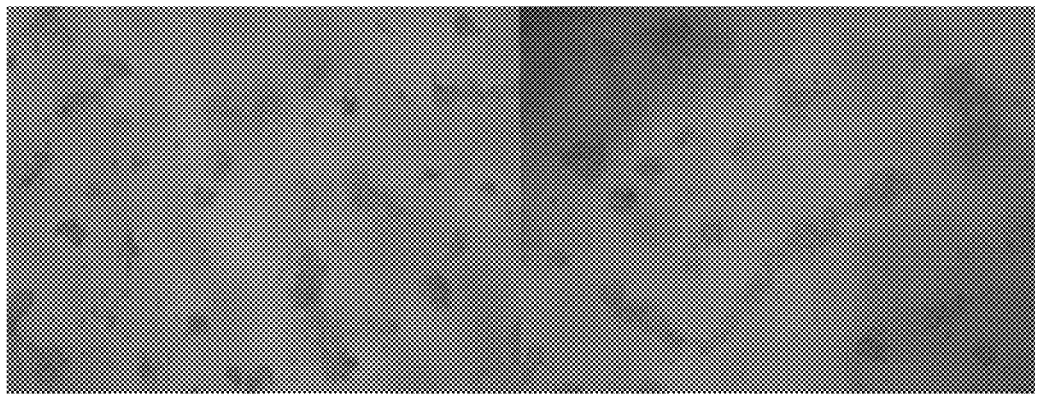
FIG. 37 are images of Equivir 150 μg/ml, added to cells 2 hours after to infection with SARS-CoV-2.
Figure 38:
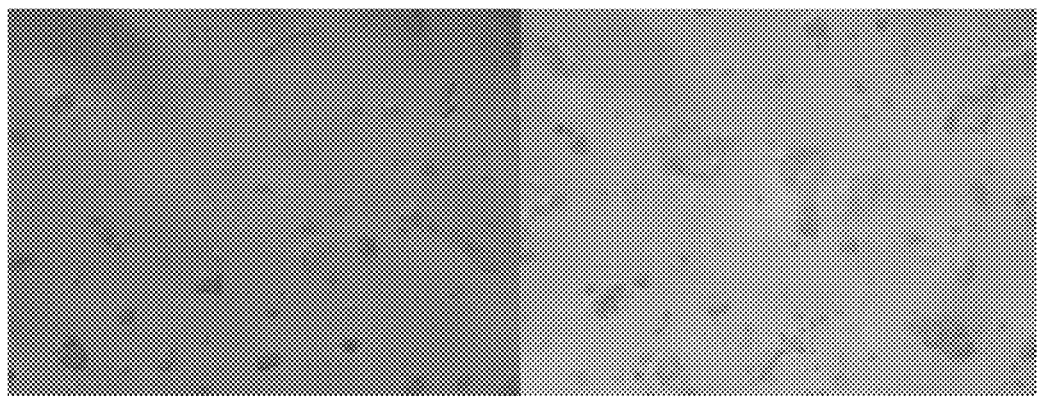
FIG. 38 are images of Equivir 100 μg/ml, added to cells 2 hours after to infection with SARS-CoV-2.
Figure 39:
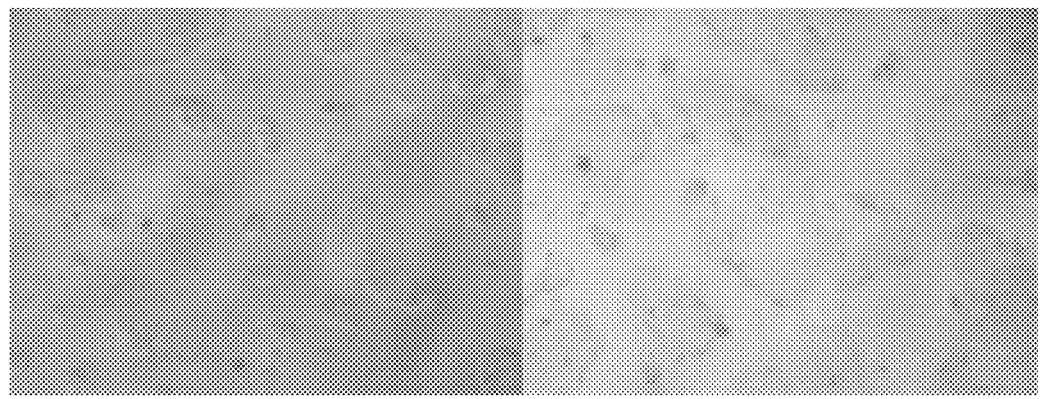
FIG. 39 are images of Equivir 50 μg/ml, added to cells 2 hours after to infection with SARS-CoV-2.
Figure 40:
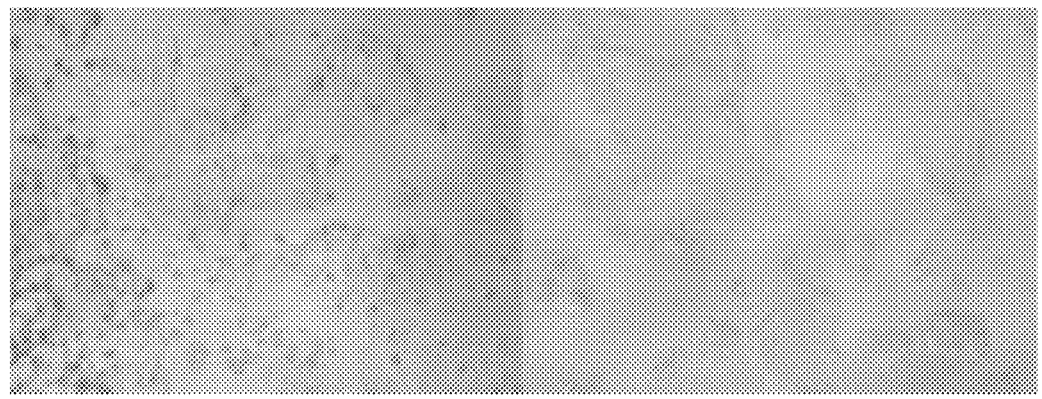
FIG. 40 are images of Equivir 25 μg/ml, added to cells 2 hours after to infection with SARS-CoV-2.
Figure 41:
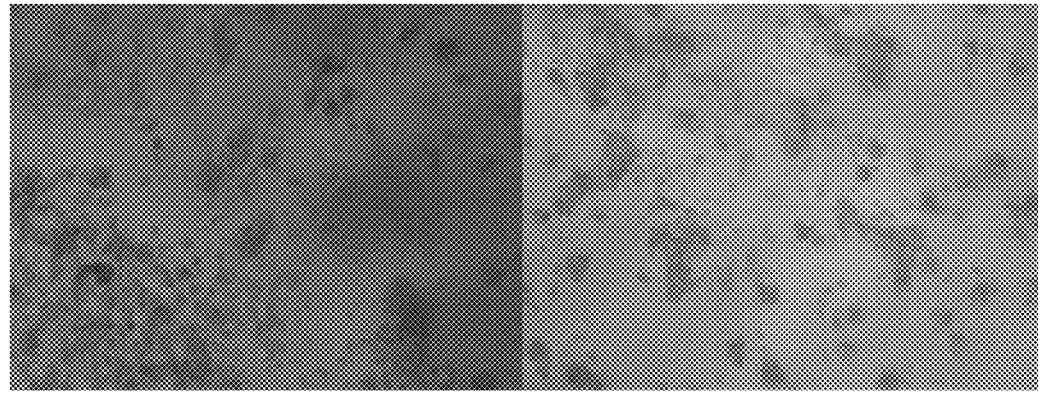
FIG. 41 are images of Equivir 200 μg/ml and gallic acid 20 μg/ml, added to cells 2 hours after to infection with SARS-CoV-2.
Figure 42:
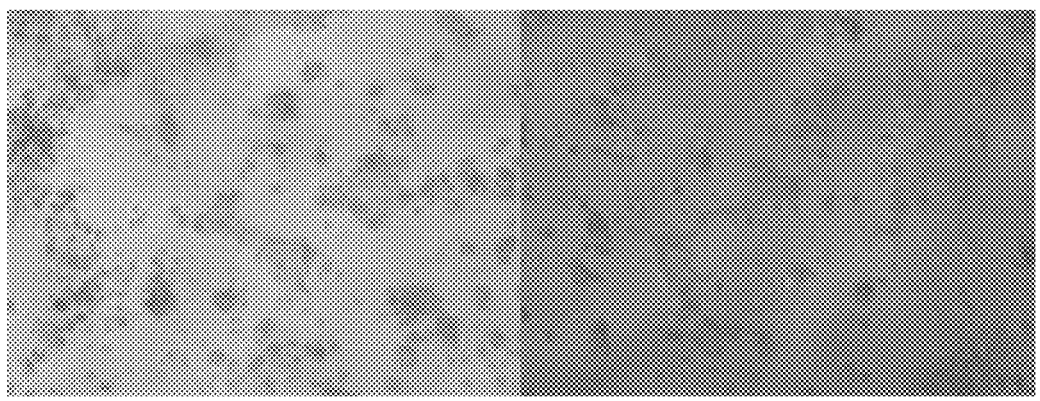
FIG. 42 are images of Equivir 150 μg/ml and gallic acid 15 μg/ml, added to cells 2 hours after to infection with SARS-CoV-2.
Figure 43:
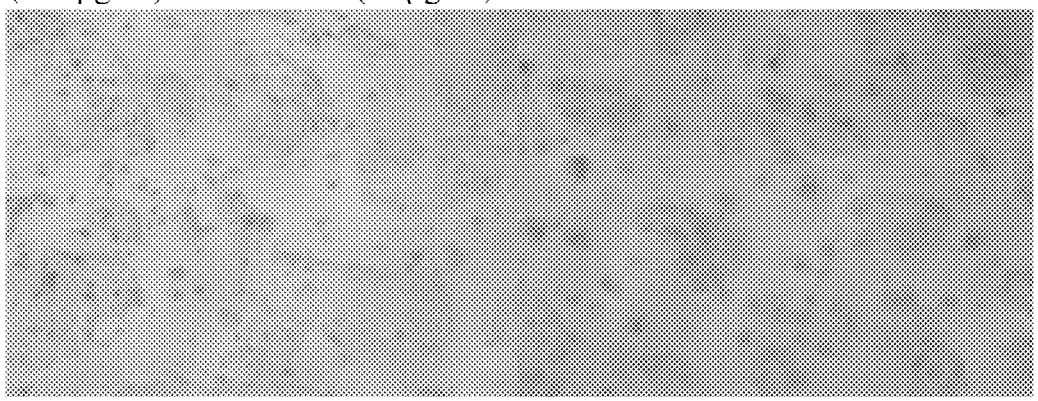
FIG. 43 are images of Equivir 100 μg/ml and gallic acid 10 μg/ml, added to cells 2 hours after to infection with SARS-CoV-2.
Figure 44:
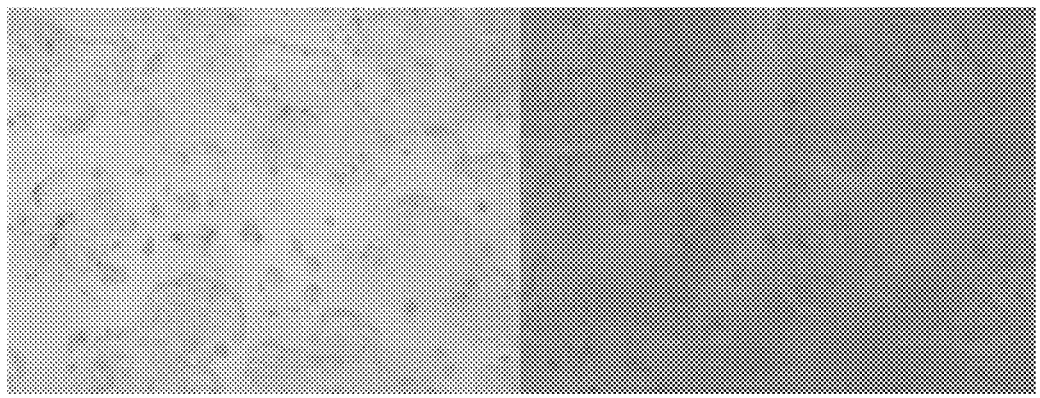
FIG. 44 are images of Equivir 50 μg/ml and gallic acid 5 μg/ml, added to cells 2 hours after to infection with SARS-CoV-2.
Figure 45:
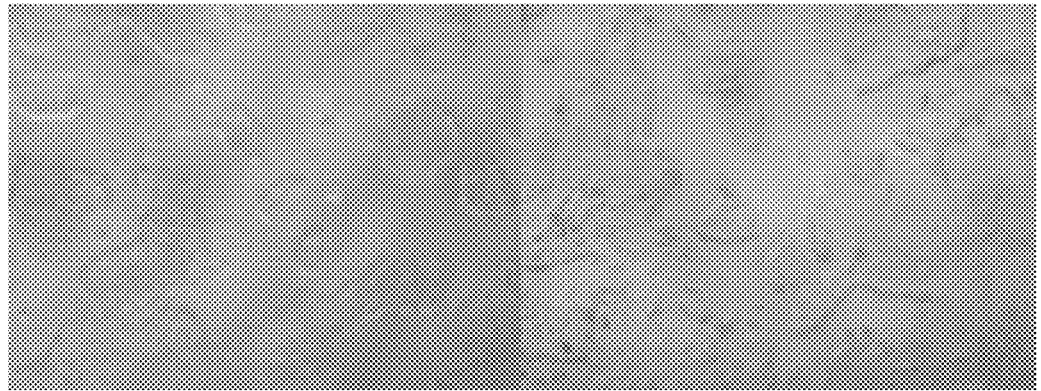
FIG. 45 are images of Equivir 25 μg/ml and gallic acid 2.5 μg/ml, added to cells 2 hours after to infection with SARS-CoV-2.
Figure 46A:
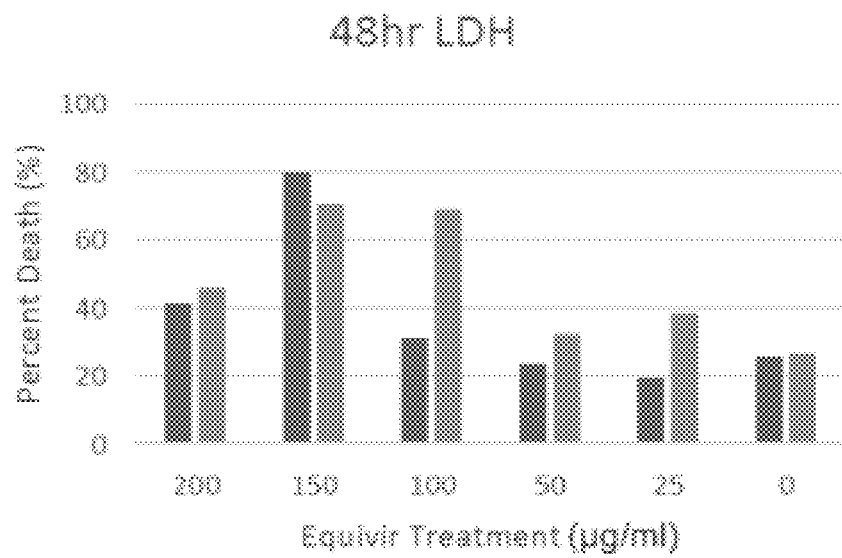
FIG. **46*a*** is a graph showing percent depth versus Equivir at 48 hours.
Figure 46B:
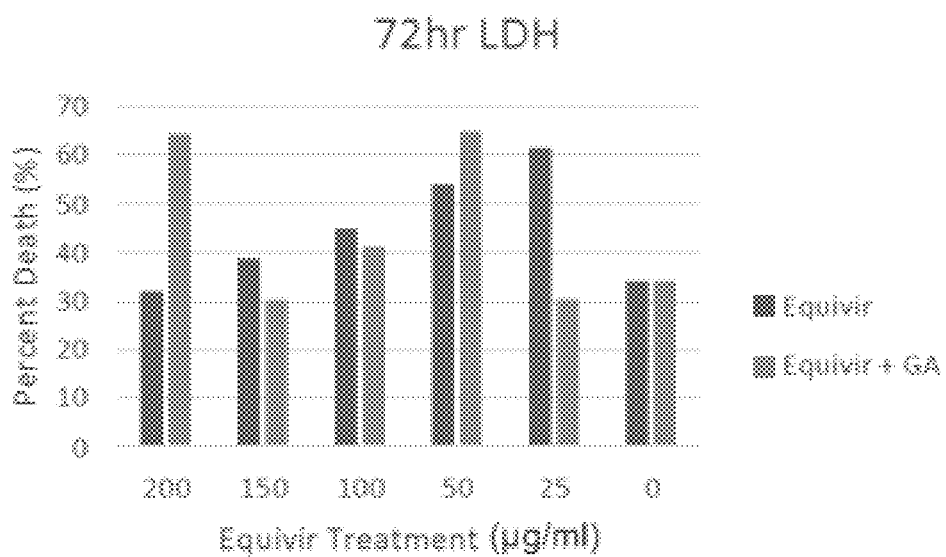
FIG. **46*b*** is a graph showing percent depth versus Equivir at 72 hours.
Figure 47:
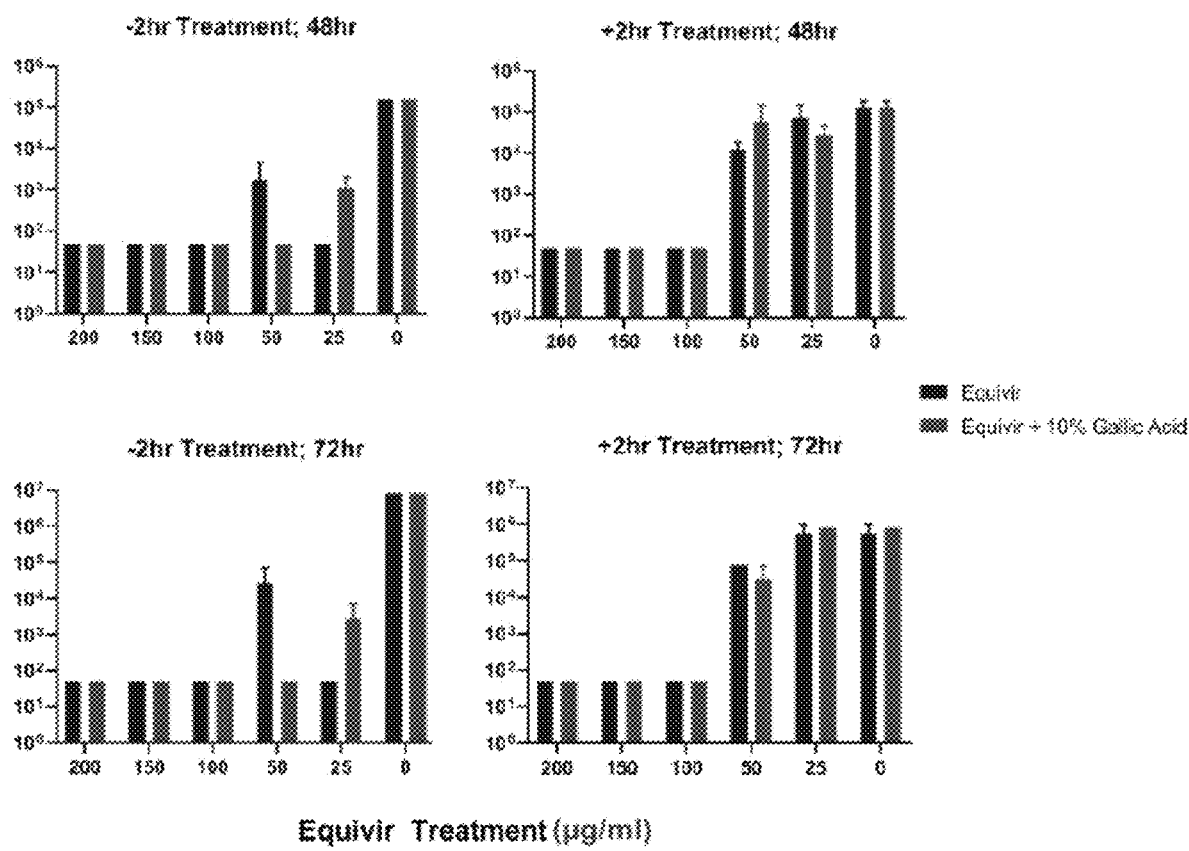
FIG. 47 includes four graphs showing SARS-CoV-2 at various concentrations and less than 2 hours or more than 2 hours for Equivir and Equivir plus 10% gallic acid.

Study #5
Objective:
To determine the toxicity of Equivir on Calu-3 cells.
Experimental Overview:
Calu-3 cells (purchased from ATCC) were seeded at a density of 1.55 cells/well in 24-well plates. Equivir was added at final concentrations of 200, 150, 100, 50, 25, and 0 µg/ml. Each concentration was tested in triplicate wells. Wells were monitored daily, and an LDH cytotoxicity assay was completed on D2 and the final day of the experiment (D3).
Concentrations of Equivir Tested:
Equivir (µg/ml): 200, 150, 100, 50, 25 and 0.
Summary of Results:
Referring to FIGS. 12 and 13, Equivir was toxic (above the control group) to Calu-3 cells at 100 µg/ml and above concentrations at 48- and 72-hours post-treatment.

Study #6
Objective:
To determine the effect of Equivir supplied by GRDG against SARS-CoV-2 in Calu-3 cells when the compound was added at the time infection. Results of this study are shown in FIGS. 14a-17.
Experimental Overview:
Calu-3 cells were seeded at a density of 5×10$^5$ cells/well in 24-well plates. Five dilutions of Equivir and vehicle treatment (DMSO) were added simultaneously with SARS-CoV-2 (MOI. 0.05). Each concentration was tested in triplicate wells. After one hour, cells were washed with PBS, and Equivir was added mentioned concentrations. Equivir was maintained in the medium throughout the infection. At 48-hour post-infection, 100 µl of supernatant was removed and viral titer in the media was quantified by TCID50 assay (protocol attached as Appendix). Representative images of each concentrations on day 3 are below.
Concentrations of Equivir Tested:
Equivir (µg/ml): 200, 150, 100, 50 and 25.
Summary of Results:
Effectiveness of Equivir against SARS-CoV-2 was tested by treating Calu-3 cells with various concentrations of Equivir added at the time of infection with a MOI of 0.05. Equivir was toxic at concentrations above 100 µg/ml and not toxic at lower concentrations. Equivir was effective in inhibiting viral replication at non-toxic concentrations of 50 µg/ml. Approximately 3- to 4-log fold reduction at 48- and 72-hours post-infection was statistically significant (One-way ANOVA). Approximately one-log fold reduction in viral titers observed at 25 µg/ml (48 hours PI) was not statistically significant.
FIGS. 14a-17 show effectiveness.

Study #7
Objective:
To determine the effect of Equivir supplied by GRDG against SARS-CoV-2 in Calu-3 cells when the compound was added either 2 hours before (−2 hr) or 2 hours after (+2 hr). Results are presented in FIGS. 18a-19b.
Experimental Overview:
Calu-3 cells were seeded at a density of 5×10$^5$ cells/well in 24-well plates. Five dilutions of Equivir and vehicle treatment (DMSO) were added to a subset of wells. Two hours after treatment (−2 hours), SARS-CoV-2 was added at MOI of 0.05. After one hour, cells were washed with PBS, and Equivir was added mentioned concentrations to the subset of wells that had previously been treated with Equivir. To rest of the wells Equivir was added 1 hour after wash (+2 hr) at indicated concentrations. Equivir was maintained in the medium throughout the infection. Each concentration was tested in triplicate wells. At 48 hours and 72 hours post-infection, 100 µl of supernatant was removed and viral titer in the media was quantified by measuring TCID50 assay (protocol is below).
Concentrations of Equivir Tested:
Equivir (µg/ml): 200, 150, 100, 50 and 25.
Summary of Results:
Effectiveness of Equivir against SARS-CoV-2 was tested by treating Calu-3 cells with various concentrations of Equivir added at 2 hours before or 2 hours after infection with a MOI of 0.05. Equivir was toxic at concentrations above 100 µg/ml and not toxic at lower concentrations.
Equivir was effective in inhibiting viral replication at non-toxic concentrations of 50 µg/ml when treated 2 hours before infection. Approximately 2 log fold reduction at 48- and 72-hours post-infection was statistically significant (One-way ANOVA). Approximately 3- to 4-fold reduction in viral titers observed at 25 µg/ml (48- and 72-hours PI).
There was no statistically significant reduction in viral replication in cells treated with Equivir 2 hours post-infection.
Limitations of the Study:
Effectiveness of the compound was tested on Calu-3 cells.
A MOI of 0.05 was tested. Therefore, effectiveness of the compounds against higher concentrations is not known.
Inhibition of viral replication by 25 µg/ml of Equivir when added 2 hours before infection needs to be repeated as subsequent confirmation by qRT-PCR does not show a similar reduction in viral titers (STUDY #8 below).

Study #8
Objective:
To determine the effect of Equivir supplied by GRDG against SARS-CoV-2 in Calu-3 cells by qRT-PCR.
Experimental Overview:
Calu-3 cells were seeded at a density of 5×10$^5$ cells/well in 24-well plates. Five dilutions of Equivir and vehicle treatment (DMSO) were added to a subset of wells. 2 hours after treatment (−2 hours), SARS-CoV-2 was added at MOI of 0.05. Equivir was added to another subset of wells at the time of infection (0 hr). After one hour, cells were washed with PBS, and Equivir was added at mentioned concentrations to the subset of wells that had previously been treated with Equivir. To rest of the wells Equivir was added 1 hour after wash (+2 hr) at indicated concentrations. Equivir was maintained in the medium throughout the infection. Each concentration was tested in triplicate wells. At 72 hours post-infection, 800 μl of supernatant was removed, RNA isolated, and viral titer in the media was quantified by qRT-PCR (protocol attached as Appendix).

Concentrations Equivir Tested:
Equivir (μg/ml): 200, 150, 100, 50, and 25.

Summary of Results:

Effectiveness of Equivir against SARS-CoV-2 was tested by treating Calu-3 cells with various concentrations of Equivir added at the time of infection, 2 hours before or 2 hours after infection with a MOI of 0.05. Equivir was toxic at concentrations above 100 μg/ml and not toxic at lower concentrations.

Equivir was effective in inhibiting viral replication at non-toxic concentrations of 50 μg/ml when treated 2 hours before infection or at the time of infection. Approximately 2 log fold reduction at 72-hours post-infection was statistically significant (One-way ANOVA). No significant reduction in viral copies was noted at 25 μg/ml concentration.

There was no statistically significant reduction in viral replication in cells treated with Equivir 2 hours post-infection at 50 and 25 μg/ml concentrations.

Study #9

Objective:

To determine the effect of Equivir against SARS-CoV-2 in Calu-3 cells by Immunofluorescence.

Experimental Overview:

Calu-3 cells were seeded at a density of $5\times10^5$ cells/well in 24-well plates upon a glass coverslip. Three dilutions of Equivir and vehicle treatment (DMSO) were added to a subset of wells. Immediately after adding the compound, SARS-CoV-2 was added at MOI of 0.05. After one hour, cells were washed with PBS, and Equivir was added at mentioned concentrations to the subset of wells that had previously been treated with Equivir. Equivir was maintained in the medium throughout the infection. At 48 hours post-infection, all supernatant was removed, cells fixed, and tested for (presence of viral antigens (NP protein) by Immunofluorescence. (protocol attached as Appendix).

Concentrations Equivir Tested:
Equivir (μg/ml): 75, 50, and 25.

Summary of Results:

Effectiveness of Equivir against SARS-CoV-2 at sub-toxic level was tested by treating Calu-3 cells with various concentrations of Equivir added at the time of infection.

A significantly lower antigen level was detected in cells treated with 50 μg/ml Equivir suggesting significantly reduced viral replication when compared to controls cells infected with SARS-CoV-2.

Limitations of the Study:

Effectiveness of the compound was tested on Calu-3 cells.

A MOI of 0.05 was tested. Therefore, effectiveness of the compounds against higher concentrations is not known.

Immunofluorescence imaging for cells treated with Equivir concentrations at 75 μg/ml and 25 μg/ml is pending (will image if required).

Overall Summary of the Studies:

Equivir is not toxic to Calu-3 cells at concentrations below 100 μg/ml.

Equivir is effective in inhibiting SARS-CoV-2 at a MOI of 0.05 in Calu-3 cells at a dose of 50 μg/ml when the virus and the drug is added at the same time as measured by TCID50 at 48- and 72-hours infection.

Equivir is effective in inhibiting SARS-CoV-2 at a MOI of 0.05 in Calu-3 cells at a dose of 50 μg/ml when the drug is added 2 hours before the virus as measured by TCID50 at 48- and 72-hours infection.

Equivir is effective in inhibiting SARS-CoV-2 at a MOI of 0.05 in Calu-3 cells at a dose of 50 μg/ml when the virus and the drug is added at the same time as measured by qRT-PCR at 72-hours infection.

Equivir is effective in inhibiting SARS-CoV-2 at a MOI of 0.05 in Calu-3 cells at a dose of 50 μg/ml when the drug is added 2 hours before virus as measured by qRT-PCR at 72-hours infection.

Less viral antigens were observed in Calu-3 cells that was treated with Equivir at 50 μg/ml when the virus and the drug is added at the same time as measured by Immunofluorescence.

Study #10

Experimental Overview:

Calu-3 cells were seeded at a density of $1.5\times10^5$ cells/well in 24-well plates. Specified wells were given pre-designated treatments of Equivir/Equivir+Gallic Acid either 2 hours prior to or following infection with SARS-CoV-2. Cells were washed and fresh media with treatment was added following infection. Supernatant was harvested and wells were imaged at 48 and 72 hr PI. TCID50 analyses were performed for each treatment condition to determine recoverable concentration of infectious virus following treatment, and LDH analysis was conducted for uninfected, treated wells to determine cytotoxicity of the treatment to Calu-3 cells. Results are shown in FIGS. 24-47.

For the purposes of promoting an understanding of the principles of the invention, the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

The invention claimed is:

1. A method of limiting the occurrence of, reducing the risk or severity of or treating a viral infection, the method comprising administering a composition comprising therapeutically effective amounts of myricetin and hesperidin to a patient at risk of or diagnosed with the viral infection selected from the group consisting of influenza, Ebola, and rhinovirus.

2. The method of claim 1, wherein the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

3. The method according to claim 1, wherein the patient is a human.

4. The method of claim 1, wherein about 300 to about 700 mg myricetin and about 100 to about 500 mg hesperidin are present in the composition.

5. The method of claim 1, wherein about 450 to about 600 mg myricetin and about 250 to about 400 mg hesperidin are present in the composition.

6. The method of claim 1, wherein about 55 to about 75% weight myricetin and about 30 to about 50% hesperidin based on the total weight of the mixture, is present in the composition.

7. The method of claim 1, wherein the ratio of myricetin to hesperidin present in the composition is about (30-60):(30-60).

8. The method of claim 1, wherein the virus is SARS COV 2 influenza.

9. The method of claim 1, wherein the composition further comprises piperine.

10. The method of claim 1, wherein the virus is rhinovirus.

11. The method of claim 1, wherein the virus is Ebola.

* * * * *